US010933415B2

(12) United States Patent
Kouge et al.

(10) Patent No.: US 10,933,415 B2
(45) Date of Patent: Mar. 2, 2021

(54) ANALYSIS CONTAINER

(71) Applicant: PHC HOLDINGS CORPORATION, Tokyo (JP)

(72) Inventors: Masahiro Kouge, Ehime (JP); Fumiya Matsubara, Ehime (JP)

(73) Assignee: PHC HOLDINGS CORPORATION, Tokyo (JP)

(*) Notice: Subject to any disclaimer, the term of this patent is extended or adjusted under 35 U.S.C. 154(b) by 339 days.

(21) Appl. No.: 15/759,374

(22) PCT Filed: Aug. 10, 2016

(86) PCT No.: PCT/JP2016/073571
§ 371 (c)(1),
(2) Date: Mar. 12, 2018

(87) PCT Pub. No.: WO2017/047297
PCT Pub. Date: Mar. 23, 2017

(65) Prior Publication Data
US 2018/0207635 A1 Jul. 26, 2018

(30) Foreign Application Priority Data

Sep. 15, 2015 (JP) ................................. 2015-181615
Sep. 15, 2015 (JP) .............................. JP2015-181614
(Continued)

(51) Int. Cl.
*B01L 3/00* (2006.01)
*G01N 35/00* (2006.01)
(Continued)

(52) U.S. Cl.
CPC ... *B01L 3/502723* (2013.01); *B01L 3/502738* (2013.01); *G01N 1/38* (2013.01);
(Continued)

(58) Field of Classification Search
CPC ......... B01L 3/502723; B01L 3/502738; B01L 2400/0409; B01L 2400/0688;
(Continued)

(56) References Cited

U.S. PATENT DOCUMENTS 6,319,469 B1 * 11/2001 Mian .................... B01F 13/0059
422/63
2007/0025876 A1 * 2/2007 Nishijima ........... B01L 3/50273
422/64
(Continued)

FOREIGN PATENT DOCUMENTS

JP     2007-315832     12/2007
JP     2009-2933     1/2009
(Continued)

OTHER PUBLICATIONS

International Search Report dated Oct. 11, 2016 in International (PCT) Application No. PCT/JP2016/073571.
(Continued)

*Primary Examiner* — Lore R Jarrett
(74) *Attorney, Agent, or Firm* — Wenderoth, Lind & Ponack, L.L.P.

(57) ABSTRACT

An analysis container comprises a main body; a first chamber that is provided inside the main body and holds a liquid sample; a second chamber; a liquid passage; and an air passage. The liquid passage connects the first chamber and the second chamber, and moves the liquid sample from the first chamber to the second chamber. The air flow chamber connects the first chamber and the second chamber, and moves air from the second chamber to the first chamber.

13 Claims, 22 Drawing Sheets

(30) Foreign Application Priority Data

| Sep. 15, 2015 | (JP) | JP2015-181619 |
|---|---|---|
| Sep. 15, 2015 | (JP) | JP2015-181620 |
| Sep. 15, 2015 | (JP) | JP2015-181675 |
| Sep. 15, 2015 | (JP) | JP2015-181676 |

(51) Int. Cl.
*G01N 37/00* (2006.01)
*G01N 1/38* (2006.01)
*C12M 1/00* (2006.01)

(52) U.S. Cl.
CPC ....... *G01N 35/00* (2013.01); *G01N 35/00029* (2013.01); *G01N 37/00* (2013.01); *B01L 2200/0684* (2013.01); *B01L 2200/10* (2013.01); *B01L 2300/087* (2013.01); *B01L 2300/0864* (2013.01); *B01L 2300/0867* (2013.01); *B01L 2400/0406* (2013.01); *B01L 2400/0409* (2013.01); *B01L 2400/06* (2013.01); *B01L 2400/0688* (2013.01); *C12M 1/00* (2013.01); *G01N 2035/00158* (2013.01); *G01N 2035/00247* (2013.01); *G01N 2035/00465* (2013.01)

(58) Field of Classification Search
CPC ......... B01L 2200/0684; B01L 2400/06; B01L 2300/0867; B01L 2300/0864; B01L 2200/10; B01L 2400/0406; B01L 2300/087; G01N 37/00; G01N 35/00; G01N 35/00029; G01N 1/38; G01N 2035/00465; G01N 2035/00247; G01N 2035/00158; C12M 1/00
See application file for complete search history.

(56) References Cited

U.S. PATENT DOCUMENTS

| 2007/0125942 | A1 | 6/2007 | Kido | |
|---|---|---|---|---|
| 2009/0169430 | A1 | 7/2009 | Yamamoto et al. | |
| 2010/0135859 | A1* | 6/2010 | Sa | B01F 15/0233 422/400 |
| 2010/0307595 | A1* | 12/2010 | Mark | B01L 3/50273 137/1 |
| 2012/0295781 | A1 | 11/2012 | Amasia et al. | |
| 2016/0144362 | A1* | 5/2016 | Lee | B01L 3/50273 436/175 |
| 2016/0214104 | A1* | 7/2016 | Schwemmer | B01L 3/502715 |

FOREIGN PATENT DOCUMENTS

| JP | 4619224 | 11/2010 |
|---|---|---|
| WO | 2007/116909 | 10/2007 |
| WO | 2008/137997 | 11/2008 |

OTHER PUBLICATIONS

Extended European Search Report dated Jun. 1, 2018 in European Application No. 16846170.5.

Keller et al., "Automated Forensic Animal Family Identification by Nested PCR and Melt Curve Analysis on an Off-the-Shelf Thermocycler Augmented with a Centrifugal Microfluidic Disk Segment", PLOS One, vol. 10, No. 7, 2015, pp. 1-17.

Office Action dated May 11, 2020 in corresponding European Patent Application No. 16 846 170.5.

\* cited by examiner

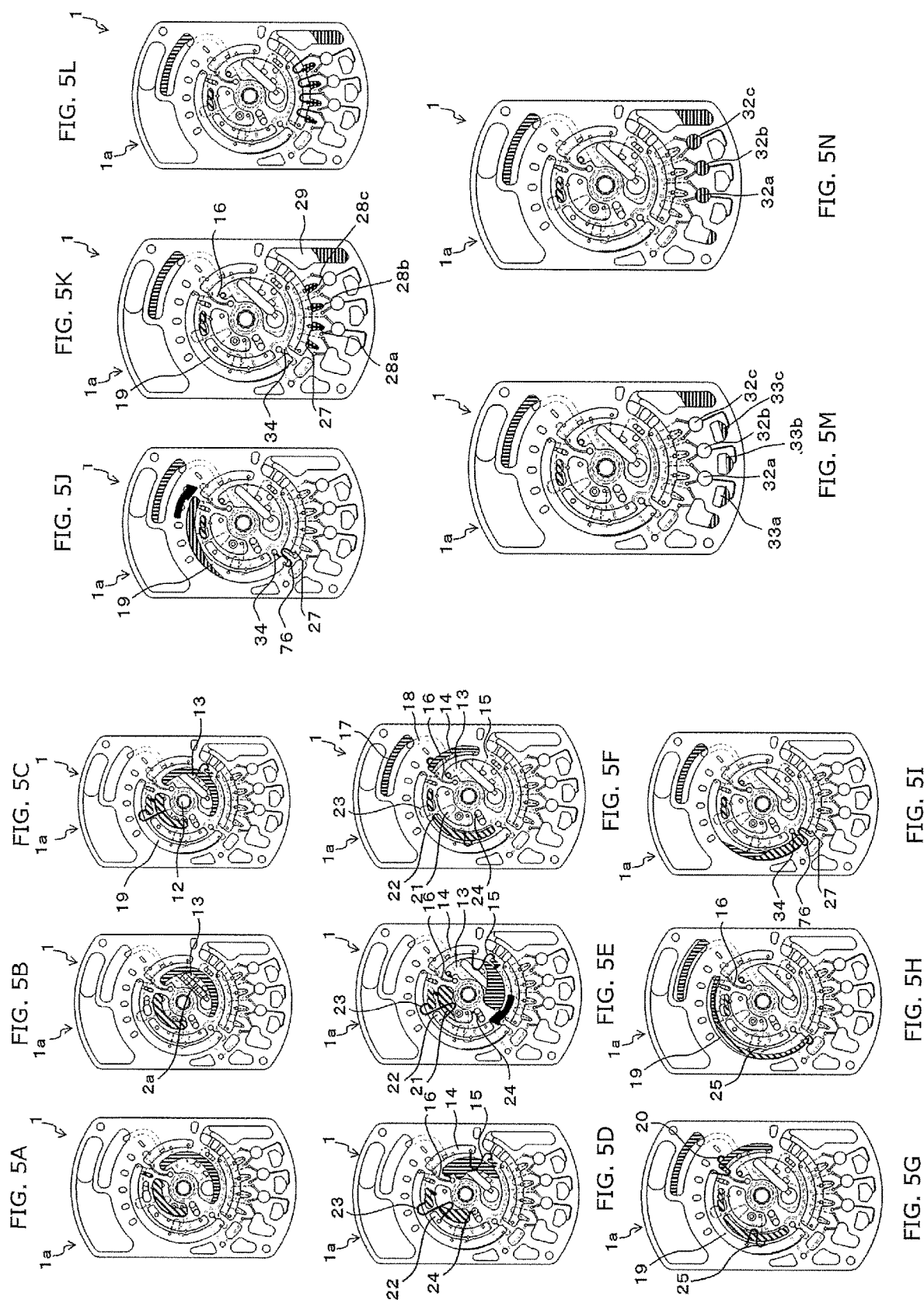

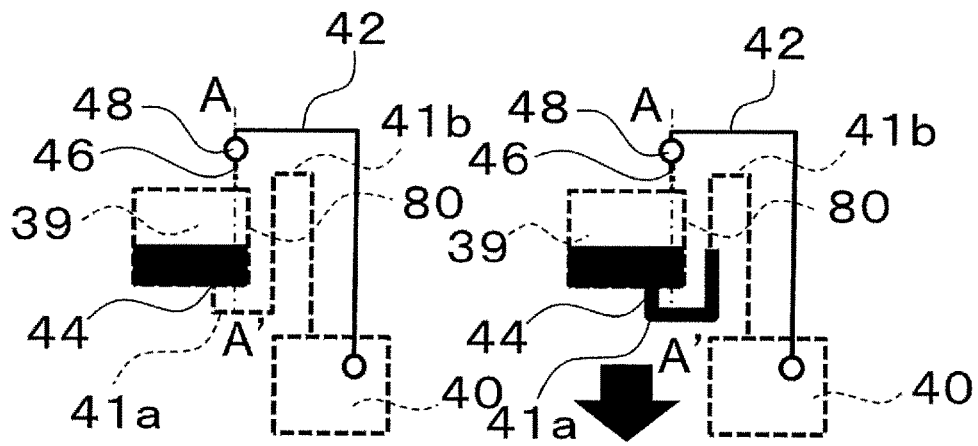
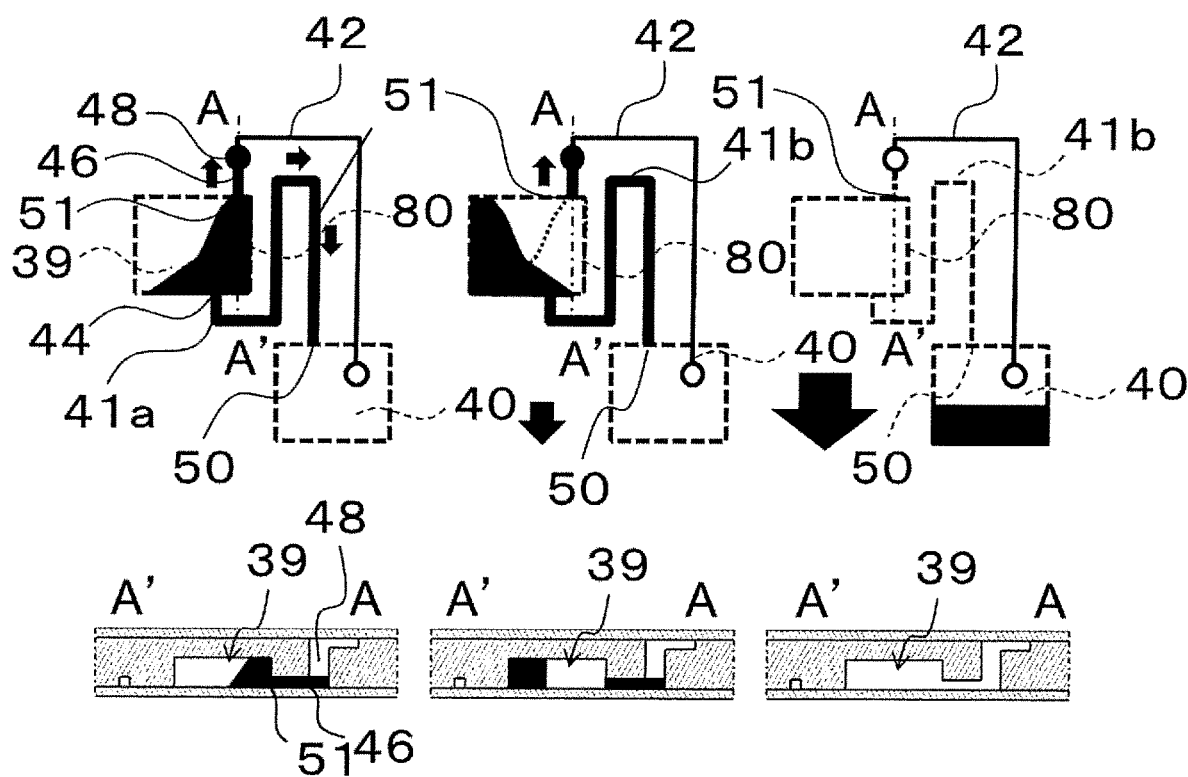
FIG. 12A  FIG. 12B
FIG. 12C  FIG. 12D  FIG. 12E

ANALYSIS CONTAINER

TECHNICAL FIELD

The present invention relates to an analysis container used for genes, for example.

BACKGROUND ART

A conventional analysis container is installed in an analysis device and used to analyze a liquid specimen that is put into the analysis container. Inside the analysis container are provided a plurality of chambers for storing and processing a liquid specimen, and passages connecting these chambers. The liquid specimen flows from chamber to chamber provided in the analysis container, through passages, and in a predetermined order, under the surface tension attributable to capillary action exerted on the passages, and the centrifugal force generated by rotating the analysis container.

For example, Patent Literature 1 discloses an analysis container configured so that a liquid specimen in an analysis container will readily flow through passages between chambers by means of air holes provided to the chambers.

CITATION LIST

Patent Literature

Patent Literature 1: Japanese Patent No. 4,619,224

SUMMARY

Technical Problem

A problem with the above-mentioned conventional example is that when the analysis container is sealed, the liquid specimen in the analysis container cannot move between chambers.

That is, with the analysis container in the above-mentioned conventional example, in order for the liquid specimen to move between chambers, it is necessary to move a quantity of air corresponding to the volume of the liquid specimen to be moved, into and out of the chambers through air holes provided in the chambers. Accordingly, with the analysis container in the above-mentioned conventional example, it is impossible to obtain a sealed state in which air cannot go in or out through the air holes.

On the other hand, when viruses are subjected to genetic analysis for the diagnosis of infectious diseases or the like, for example, it is necessary to seal the analysis container in order to prevent the release of amplified products produced in large quantities in the course of the amplification reaction. However, if the analysis container is sealed, as mentioned above, air corresponding to the volume of the liquid specimen to be moved cannot move in and out of the chamber from the outside, so the liquid specimen cannot move between the chambers.

In view of this, it is an object of the present invention to provide an analysis container with which a liquid specimen inside the analysis container can be moved between chambers even when the analysis container is sealed.

Solution to Problem

To achieve this object, the present invention comprises a main body, a first chamber that is provided inside the main body and holds a liquid sample, a second chamber, a liquid passage, and an air passage. The liquid passage connects the first chamber and the second chamber and moves the liquid sample from the first chamber to the second chamber. The air passage connects the first chamber and the second chamber and moves air from the second chamber to the first chamber.

Advantageous Effects

With the analysis container pertaining to the present invention, when the liquid sample is moved from the first chamber to the second chamber via the liquid passage, air can be moved through the air passage, from the second chamber to the first chamber, in an amount equal to the volume of liquid sample to be moved. This allows the liquid specimen in the analysis container to be moved between the chambers even in a state in which the analysis container is sealed.

BRIEF DESCRIPTION OF DRAWINGS

FIGS. 5A to 5N are analysis process diagrams of an analysis container depicting an embodiment of the present invention;

FIGS. 12A to 12E show top views of the main components of an analysis container depicting an embodiment of the present invention in the upper parts, and show cross sections along the A-A' line in the lower parts;

FIGS. 15A and 15B show cross sections along the A-A' line in the lower parts;

DETAILED DESCRIPTION OF EMBODIMENTS

A configuration in which the analysis container pertaining to an embodiment of the present invention is applied to a genetic analysis container will now be described through reference to the appended drawings.

In the following description, the terms "inner peripheral side" and "outer peripheral side" respectively refer to the inner peripheral side and outer peripheral side of a circle in which a rotary shaft insertion hole 12 (discussed below) is the center of rotation.

Embodiment 1

Figure 1A:
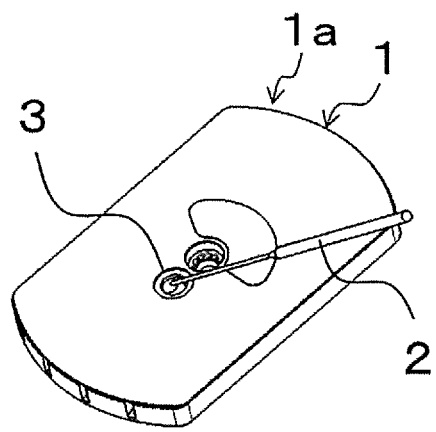
FIG. 1A to 1D are process diagrams of an analysis container depicting an embodiment of the present invention.

FIG. 1A is an oblique view of the configuration of an analysis container 1 in this embodiment.

The analysis container 1 is used, for example, for analyzing genes.

As shown in FIG. 1A, the user inserts a swab 2 onto which a sample has been collected into the insertion opening 3 of the main body 1a of the analysis container 1. The user then cuts off the tip portion 2a (the specimen collection portion) of the swab 2, and puts it into the main body 1a of the analysis container 1.

Figure 1B:
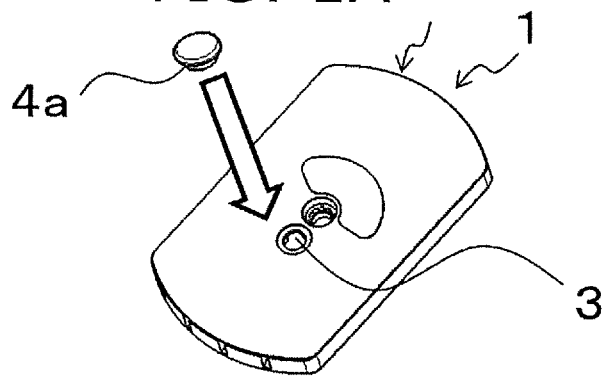
Figure 1C:
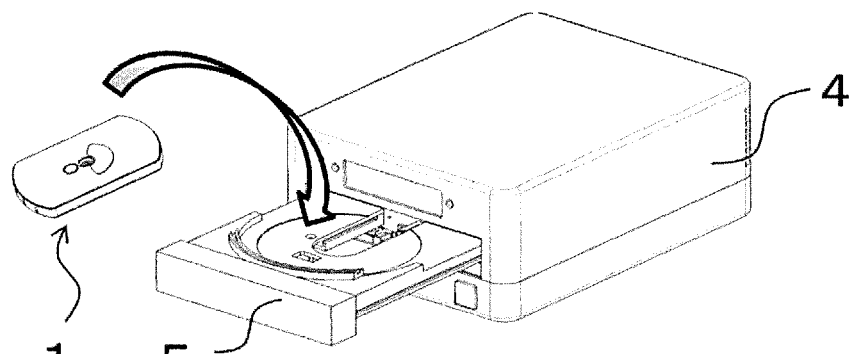

Then, as shown in FIG. 1B, the user places the cap (lid) 4a over the insertion opening 3 and puts the analysis container 1 on an analysis container loading tray 5 of a measuring device 4.

Figure 1D:
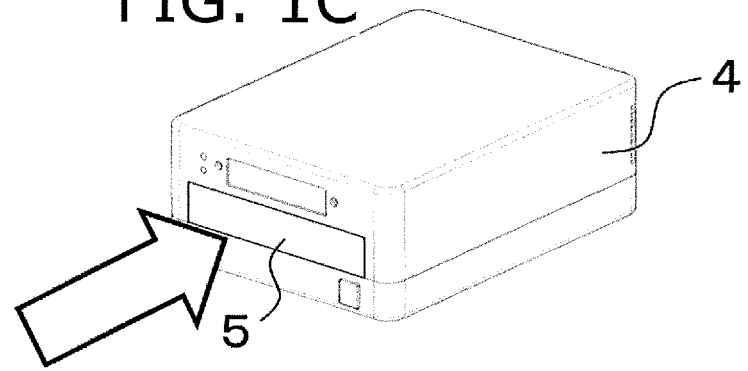

After this, as shown in FIG. 1D, the user closes the analysis container loading tray 5 and sets the analysis container 1 in the measuring device 4.

The analysis container 1 will be described in detail below, but the specimen poured in through the insertion port 3 is split up into a plurality of chambers by a branching path constituted by passages, is reacted with a reagent in each chamber, and genetic analysis is performed according to the reaction situation.

FIGS. 2A to 2C and FIGS. 3A to 3C show the process of manufacturing the analysis container 1.

Figure 2A:
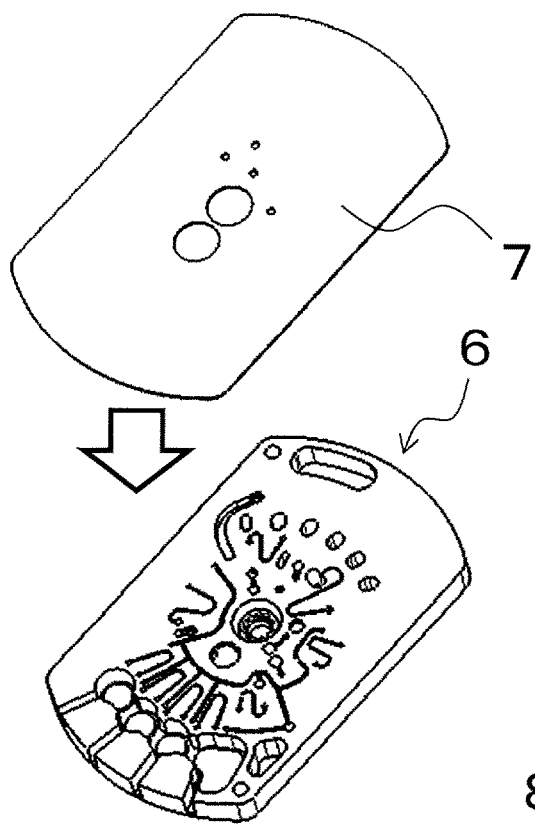
FIGS. 2A to 2C are process diagrams of an analysis container depicting an embodiment of the present invention.

As shown in FIG. 2A, an upper film 7 is thermally welded to the upper surface of the analysis container base 6 of the analysis container 1. Specific examples of this thermal welding include laser welding and ultrasonic welding.

Figure 2B:
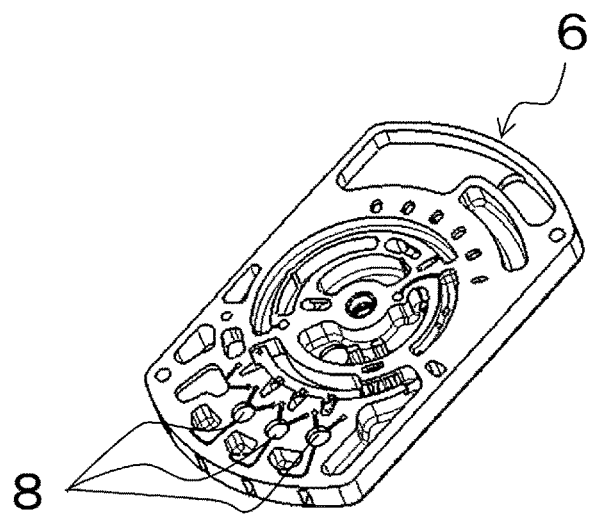

Next, as shown in FIG. 2B, a dry reagent is applied to a particular chamber 8 on the lower surface side of the analysis container base 6.

Figure 2C:
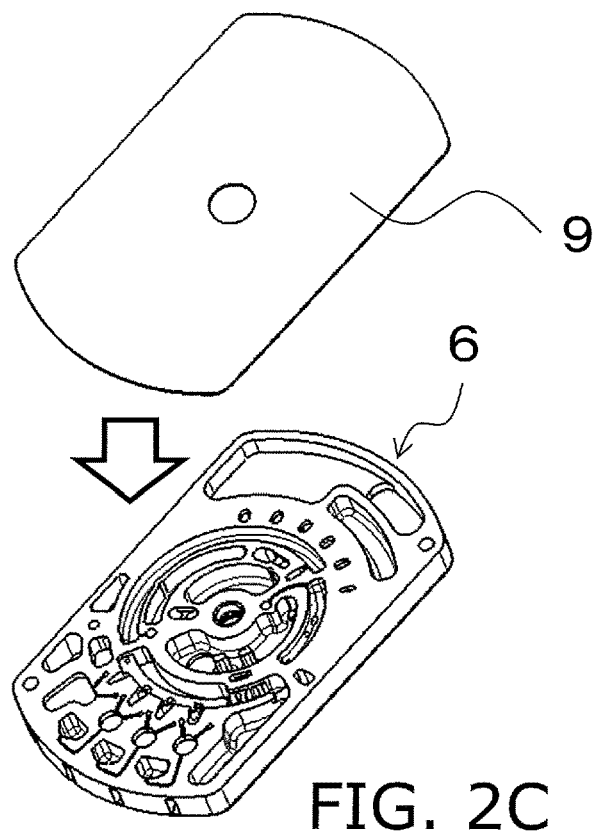

Then, as shown in FIG. 2C, a lower film 9 is thermally welded to the lower surface side of the analysis container base 6.

Figure 3A:
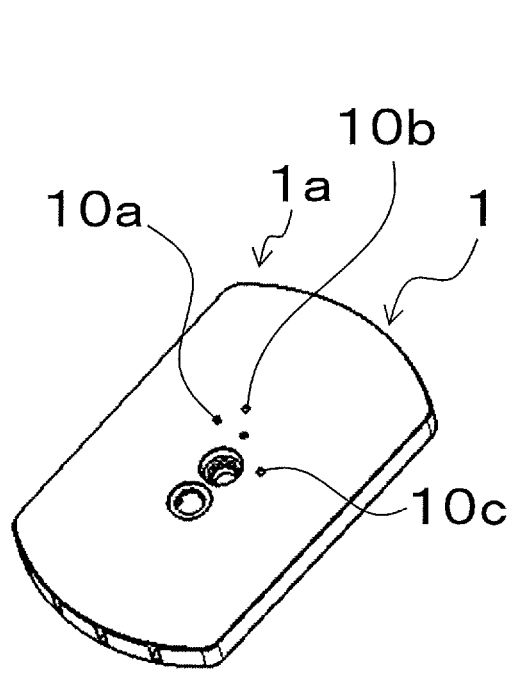
FIGS. 3A to 3C are process diagrams of an analysis container depicting an embodiment of the present invention.

Next, as shown in FIG. 3A, the upper film 7 is provided with filling ports 10a, 10b, and 10c for reagent solutions. 400 uL of the specimen extract is then poured into the filling port 10a, 10 uL of an inhibitor/moderator is poured into in the filling port 10b, and 477 uL of a specimen diluent is poured into the filling port 10c.

Figure 3B:
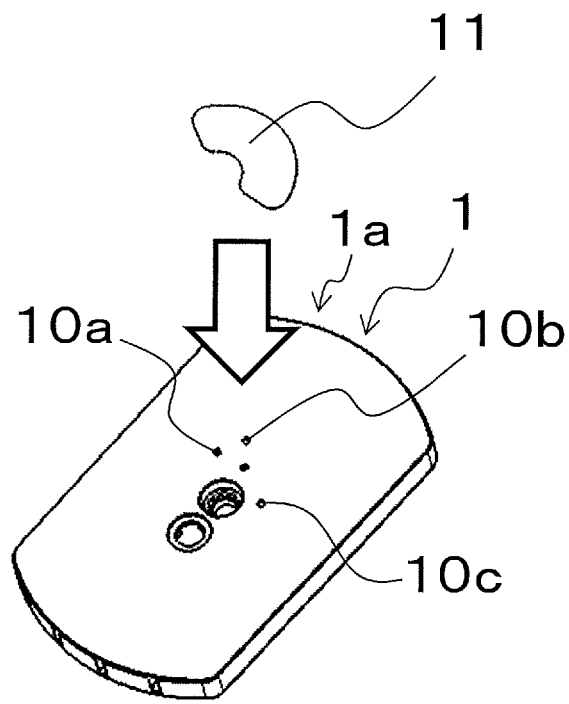
Figure 3C:
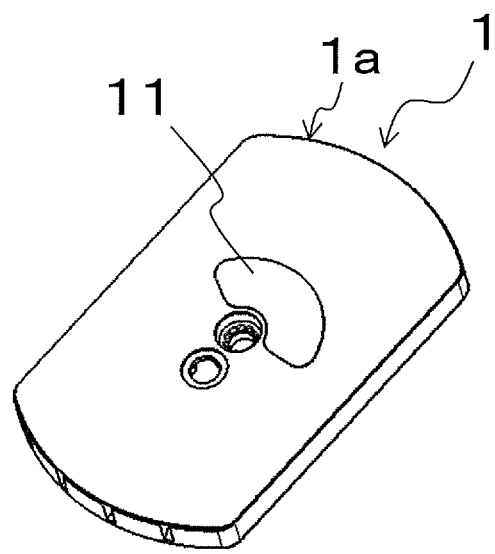

Then, as shown in FIG. 3B, after the filling ports 10a, 10b, and 10c have been filled with the reagent solutions, a sealing member 11 is affixed by thermal welding, with an adhesive agent, or the like so as to block off the reagent solution filling ports 10a, 10b, and 10c. This completes the analysis container 1 having the reagent, as shown in FIG. 3C.

Configuration of Chambers and Passages in Analysis Container 1

Figure 4B:
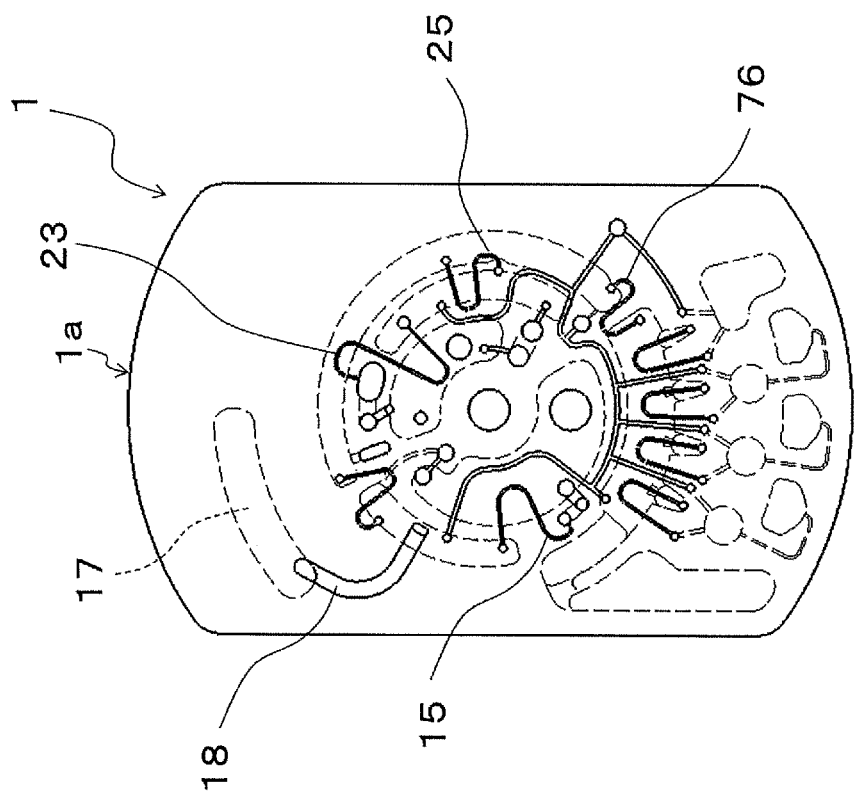
FIGS. 4A and 4B are a bottom view and a top view of an analysis container depicting an embodiment of the present invention.
Figure 4A:
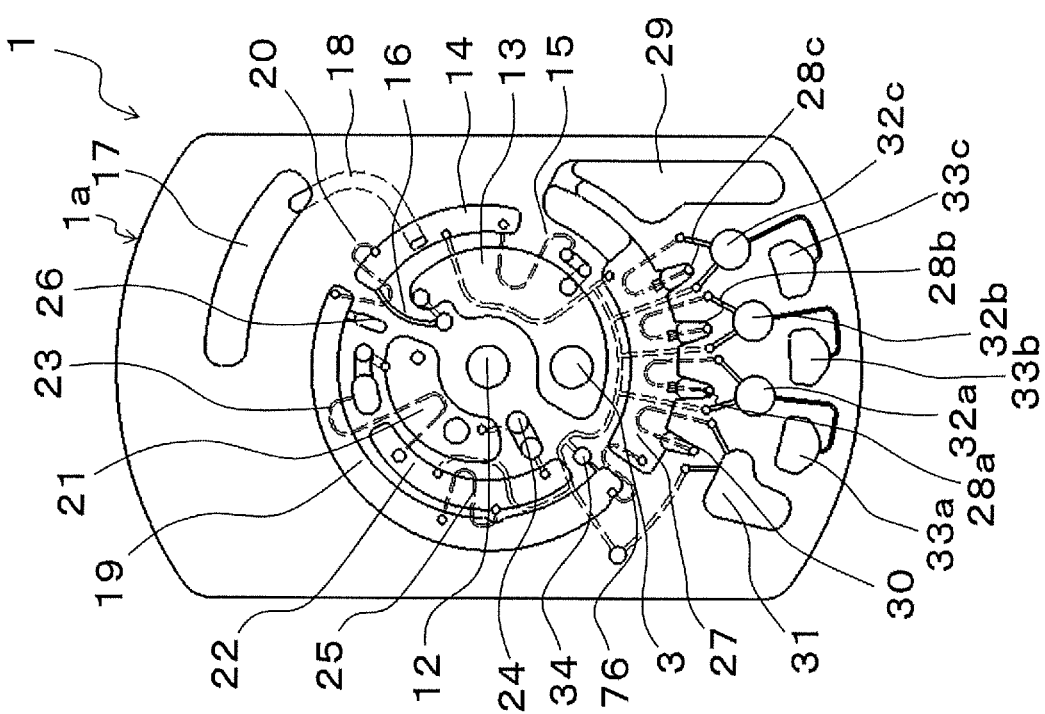

FIGS. 4A and 4B show the chambers and passages provided in the main body 1a of the analysis container 1.

FIG. 4A is an oblique view of the bottom face of the main body 1a of the analysis container 1. Solid lines indicate the chambers and passages provided on the lower face side, and dotted lines indicate the chambers and passages provided on the upper face side.

FIG. 4B is an oblique view of the top face. Solid lines indicate chambers and passages provided on the upper face side, and dotted lines indicate chambers and passages provided on the lower face side.

In the lower-face oblique view shown in FIG. 4A, a rotary shaft provided in the measuring device 4 is inserted into the rotary shaft insertion hole 12, which is provided substantially in the center of the main body 1a. This keeps the analysis container 1 in the state of being able to rotate and pivot in the measuring device 4. The main body 1a is provided with the insertion opening 3, into which a specimen is inserted.

As mentioned above, the specimen is inserted through the insertion opening 3 in a state of adhering to the cut tip 2a of the swab 2. A specimen extraction chamber 13 that has been filled with an extract is provided under the insertion opening 3.

A specimen quantification chamber 14 is provided on the outer peripheral side of the specimen extraction chamber 13. The specimen extraction chamber 13 and the specimen quantification chamber 14 are connected by a liquid passage 15 and a vent passage (air passage) 16.

An overflow chamber 17 is provided around the outer periphery of the specimen quantification chamber 14, and is connected by a passage 18.

Also, the specimen quantification chamber 14 quantifies the specimen extract in the specimen extraction chamber 13 so as to have a particular volume. After the specimen extract is quantified in the specimen quantification chamber 14, any excess specimen extract is collected in the overflow chamber 17.

The specimen quantification chamber 14 is also connected to a mixing chamber 19 by a capillary passage 20.

The configuration of the passages and chambers of the specimen extract from the specimen extraction chamber 13 to the mixing chamber 19 was described above.

Next, the configuration of the passages and chambers of the specimen extract from a specimen dilution chamber 21 to the mixing chamber 19 will be described.

The specimen dilution chamber 21 is provided on the inner peripheral side of the analysis container 1 near the rotary shaft insertion hole 12.

A blank chamber 22 is provided on the outer peripheral side of the specimen dilution chamber 21, and the specimen dilution chamber 21 and the blank chamber 22 are connected via a liquid passage 23 and a vent passage 24.

The blank chamber 22 is also connected to the mixing chamber 19 by a capillary passage 25.

The configuration of the passages and chambers of the specimen diluent from the specimen dilution chamber 21 to the mixing chamber 19 was described above.

The mixing chamber 19 is connected to a reagent loading chamber 26 via a passage. The reagent loading chamber 26 is prefilled with an inhibitor/moderator. That is, the specimen extract, the specimen diluent, and the inhibitor/moderator are mixed in the mixing chamber 19.

The mixed liquid obtained in the mixing chamber 19 goes through a capillary passage 76 and enters a dispensing chamber 27. After this, the mixture flows into a plurality of quantitative chambers 28a, 28b, and 28c and is quantified to a liquid amount that is the same as a predetermined chamber volume. Any surplus mixture enters an overflow chamber 29.

Here, the mixture remaining in the mixing chamber 19 sometimes flows in after being quantified in the quantification chambers 28a, 28b, and 28c. If this happens, it will be difficult to perform accurate quantification in the quantification chambers 28a, 28b, and 28c, and the subsequent reaction can not be carried out accurately. Therefore, a trap chamber 30 and a reservoir 31 that is connected by a passage to the trap chamber 30 are provided on the upstream side of the quantification chambers 28a, 28b, and 28c.

Consequently, an accurate reaction can be carried out without impeding the quantification in the quantification chambers 28a. 28b, and 28c.

The mixtures quantified in the quantification chambers 28a, 28b, and 28c come into contact with the dry reagent in the reaction chambers 32a, 32b, and 32c, are stirred in pump chambers 33a, 33b, and 33c, and are thereby mixed with the dry reagent.

Analysis Process of Analysis Container 1

FIGS. 5A to 5N show the analysis process when the analysis container 1 is installed in the measurement device 4.

The analysis process comprises the preliminary preparation step shown in FIG. 5A, the preprocessing steps shown in FIGS. 5B to 5E, the mixing steps shown in FIGS. 5F to 5J, and the reaction steps shown in FIGS. 5K to 5N.

DESCRIPTION OF PRELIMINARY PREPARATION STEP

First, as shown in FIG. 5A, the preliminary preparation step is carried out by using the reagent solution filling ports 10a, 10b, and 10c (not numbered in the drawing) provided to the main body 1a of the analysis container 1. That is, as described above, the filling port 10a is filled with 400 uL of the specimen extract. The filling port 10b is then filled with 10 uL of the inhibitor/moderator. The filling port 10c is filled with 477 uL of the specimen diluent in advance.

Description of Pretreatment Step

The pretreatment step will now be described. In the pretreatment step, the tip portion 2a of the swab 2 onto which the specimen has been collected is first cut off, and this is fixed to the inner peripheral portion in the specimen extraction chamber 13 as shown in FIG. 5B.

Next, in FIG. 5C, the analysis container 1 installed in the measurement device 4 is rotated at a high speed of 3500 rpm around the rotation shaft insertion hole 12. The centrifugal force produced by this high-speed rotation removes the moisture from the specimen adhering to the tip portion 2a of the swab 2 and mixes the specimen with the extract in the specimen extraction chamber 13. Then, 10 uL of the inhibitor/moderator enters the mixing chamber 19. At this time, since the inhibitor/moderator flows into the reservoir 77 (capacity of several tens of microliters) provided to the mixing chamber 19, it does not flow downstream and remains in the mixing chamber 19.

Next, in FIG. 5D, the rotation of the analysis container 1 is abruptly stopped. Stopping the rotation of the analysis container 1 causes the sample extract to move by the capillary force through the liquid passage 15, and it stops at the terminal end on the specimen quantification chamber 14 side due to the surface tension.

At the same time, since the specimen extract enters the vent passage 16 and blocks off the passage, the specimen extract acts to stop the movement of air.

Also, when the rotation of the analysis container 1 stops, the sample diluent moves under capillary force through the liquid passage 23 and comes to a stop at the terminal end on the blank chamber 22 side due to the surface tension.

At the same time, since the specimen diluent enters the vent passage 24 and blocks off the passage, it acts to stop the movement of air.

In FIG. 5E, the analysis container 1 is shaken. Shaking the analysis container 1 stirs the specimen and the extract in the specimen extraction chamber 13. At this point, the specimen extract and specimen diluent enter the vent passages 16 and 24 and block off the passage, and thereby act to stop the movement of air. This action produces a negative pressure in the specimen extraction chamber 13 and the specimen dilution chamber 21. Accordingly, the specimen extract and the specimen diluent in the liquid passages 15 and 23 can be prevented from flowing into the specimen quantification chamber 14 or the blank chamber 22.

Description of Mixing Step

The mixing step will now be described. In the mixing step, first, as shown in FIG. 5F, the analysis container 1 is rotated at a high speed of 3500 rpm. The centrifugal force produced by this high-speed rotation causes the specimen extract liquid blocking off the vent passage 16 to be temporarily drawn into the specimen extraction chamber 13. The specimen extract is then sent through the liquid passage 15 to the specimen quantification chamber 14. The specimen extract is quantified in the specimen quantification chamber 14. Here, any excess specimen extract is sent through the passage 18 to the overflow chamber 17.

At the same time, the specimen diluent blocking the vent passage 24 is temporarily drawn into the specimen dilution chamber 21. The diluent is then sent through the liquid passage 23 to the blank chamber 22.

Next, in FIG. 5G, the rotation of the analysis container 1 is abruptly stopped. Stopping the rotation of the analysis container 1 causes the sample extract to be sent to the end of the capillary passage 20 on the mixing chamber 19 side.

Also, stopping the rotation of the analysis container 1 causes the sample diluent to be sent to the end of the capillary passage 25 on the mixing chamber 19 side.

Next, in FIG. 5H, the analysis container 1 is rotated at a high speed of 3500 rpm. The centrifugal force produced by the high-speed rotation of the analysis container 1 causes the specimen extract to go through the vent passage 16 and enter the mixing chamber 19. Then, the specimen diluent goes through the capillary passage 25 and enters the mixing chamber 19. The inhibitor/moderator has already entered the mixing chamber 19. Therefore, at this point, the three liquids, namely, the specimen extract, the specimen diluent, and the inhibitor/moderator, are inside the mixing chamber 19.

Next, in FIG. 5I, the rotation of the analysis container 1 is abruptly stopped. Stopping the rotation of the analysis container 1 causes the mixture of the three liquids, that is, the sample extract, the sample diluent, and the inhibitor/moderator, to be sent to the end of the capillary passage 76 on the dispensing chamber 27 side. At the same time, since the mixture enters the vent passage 34 and blocks off the passage, it acts to stop the movement of air.

In FIG. 5J, the analysis container 1 is shaken. Shaking the analysis container 1 stirs and mixes the three liquids in the mixing chamber 19. At this point, the mixture enters the vent passage 34 and blocks off the passage, and so acts to stop the movement of air. Since this action produces negative pressure in the mixing chamber 19, the mixture in the capillary passage 76 can be prevented from flowing into the dispensing chamber 27.

Next, in FIG. 5K, the analysis container 1 is rotated at a high speed of 3500 rpm. The centrifugal force produced by the high-speed rotation of the analysis container 1 causes the mixture blocking the vent passage 34 to be temporarily drawn into the mixing chamber 19. The mixture then goes through the vent passage 16 and is sent to the dispensing chamber 27. The mixture is quantified in the quantification chambers 28a, 28b, and 28c via the dispensing chamber 27. Here, any surplus mixture remaining after quantification is sent to the overflow chamber 29.

Next, in FIG. 5L, the rotation of the analysis container 1 is abruptly stopped. In FIG. 5M, control is performed while the rotational speed of the analysis container 1 is switched in two stages. More specifically, the rotation is controlled while switching between 5 seconds of high-speed rotation at 3000 rpm and 5 seconds of low-speed rotation at 100 rpm.

As a result, the centrifugal force changes according to the change in the rotational speed, so the mixture goes back and forth between the reaction chambers 32a, 32b, and 32c and the pump chambers 33a, 33b, and 33c connected to the outer periphery thereof. Here, the reaction chambers 32a, 32b, and 32c are loaded in advance with a dry reagent. Therefore, the liquid mixture and the dry reagent are stirred while being mixed together.

Next, as shown in FIG. 5N, the analysis container 1 is controlled at a medium-low-speed rotation of 240 rpm. During this medium-low-speed rotation, the liquid mixture is in a state of being sent to the reaction chambers 32a, 32b, and 32c on then inner peripheral side.

Thus, when the liquid mixture has entered the reaction chambers 32a, 32b, and 32c, the analysis device is controlled so that the temperature environment of the analysis container 1 will be a specific temperature. As a result, the reaction results of the reaction chambers 32a, 32b, and 32c can be optically detected by fluorescence observation or the like, for example, and the genes to be measured that are contained in the sample can be analyzed.

The basic configuration of the analysis container 1 and the analysis process using the analysis container 1 were described above, but the main features of the analysis container 1 in this embodiment will now be described in specific terms.

Description of Swab Holding Mechanism

Figure 6:
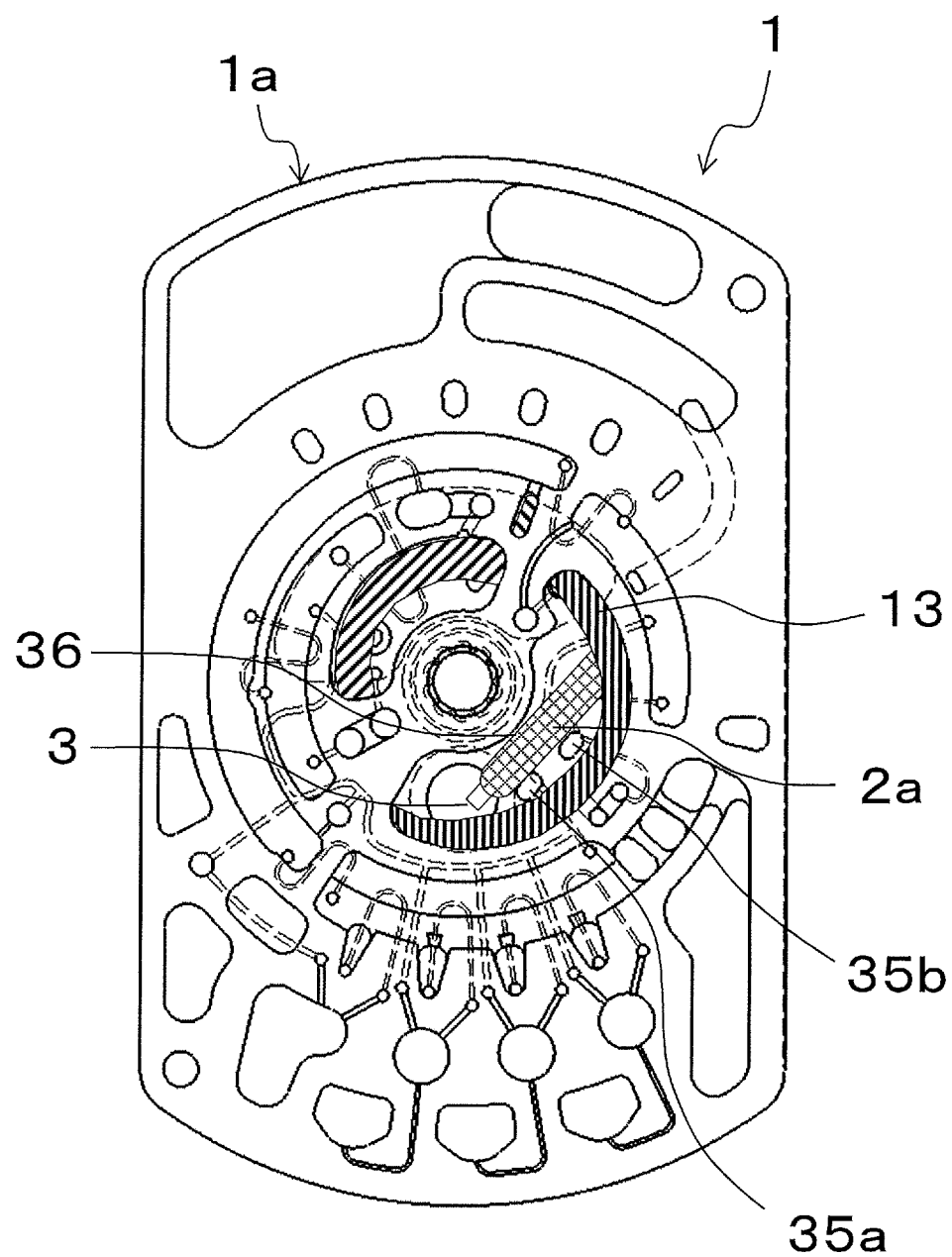
FIG. 6 is a bottom view of an analysis container depicting an embodiment of the present invention.

FIG. 6 is an oblique view of the bottom face of the analysis container 1 during the pretreatment step.

As discussed above, in the pretreatment step, first, as shown in FIG. 6, the tip portion 2a of the swab 2 onto which the specimen has been collected is cut off.

The analysis container 1 is provided with a swab holder that fixes the tip portion 2a to the inner peripheral portion in the specimen extraction chamber 13. In the specimen extraction chamber 13, the swab holder sandwiches the cut tip portion 2a of the swab 2 between protrusions (holders) 35a and 35b on the outer peripheral side and the inner walls (holder and specimen extraction chamber walls) 36 of the specimen extraction chamber 13 on the inner peripheral side. This allows the tip portion 2a to be held without moving.

Figure 7:
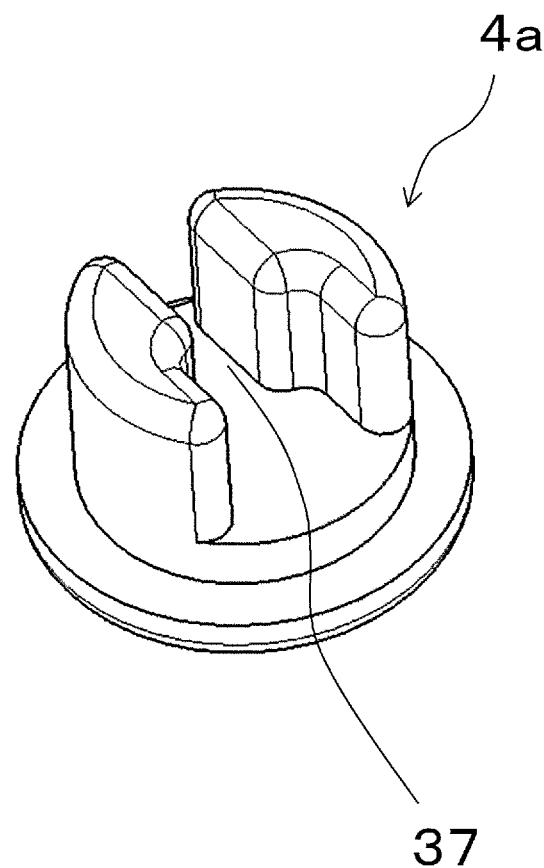
FIG. 7 is an oblique view of the main components of an analysis container depicting an embodiment of the present invention.

As shown in FIG. 7, a guide 37 for holding the rear end of the cut tip portion 2a of the swab 2 is also provided on the rear side of the cap 4a Therefore, when the analysis container 1 is rotated at high speed to dehydrate and separate the specimen collected at the tip portion 2a of the swab 2 to the outer peripheral side of the specimen extraction chamber 13 by centrifugal force, the specimen can be fixed to and held on the inner peripheral side in the specimen extraction chamber 13.

Description of Flow in Preprocessing Step

When a conventional analysis container is used, this entails performing a step of extracting the genes, such as DNA or RNA, to be measured from a specimen adhering to the specimen collector, and a step of diluting the extracted genes to an appropriate concentration with a specimen diluent. These two pretreatment steps are performed beforehand outside the reaction container, and the liquid mixture produced here is poured into the analysis container, after which it is reacted with the reagent and analyzed.

The analysis container 1 in this embodiment is configured to be capable of performing analysis steps including these pretreatment steps. A flowchart of the pretreatment steps is shown in FIG. 8.

Figure 8:
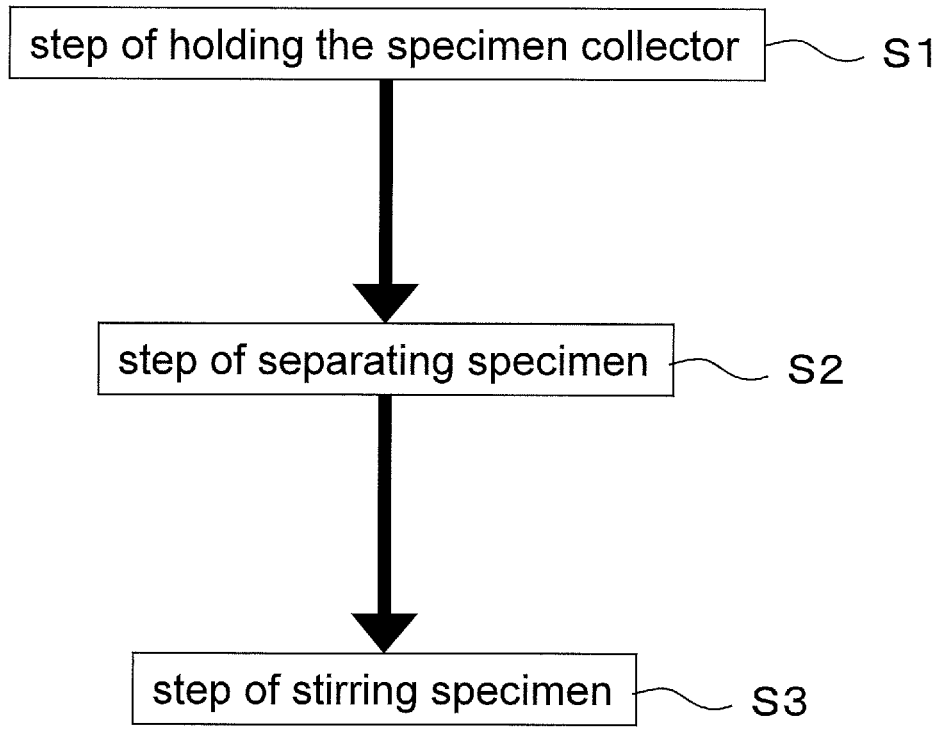
FIG. 8 is a flowchart of preprocessing steps, depicting an embodiment of the present invention.

More specifically, as shown in FIG. 8, the pretreatment step includes a holding step (S1) of holding the specimen collector in a chamber containing the specimen extract from the inside of the analysis container 1, a specimen separation step (S2) of rotating the analysis container 1 at a high speed of 3500 rpm to dehydrate and separate the specimen on the specimen collector by centrifugal force, and a stirring step (S3) of shaking the analysis container 1 to stir the extract and the specimen separated in the extract.

Description of Vent Passage

The analysis container 1 in this embodiment is used, for example, when a subject is suspected of having been infected with an infectious disease such as influenza, to identify the type of influenza. More precisely, the analysis container 1 is used for so-called gene amplification, in which influenza virus genes are amplified and their sensitivity is raised, and are then identified.

When amplifying and analyzing genes in this way, it is necessary to seal the interior of the analysis container 1 and prevent the outflow of air from the outside atmosphere (contamination) in order to prevent the release of the amplified product.

Since the analysis container 1 in this embodiment is used in a sealed state, the admixing of contaminants can be prevented. On the other hand, in order to move the liquid between the chambers in the analysis container 1, it is necessary to move air having a volume corresponding to the volume of the moved liquid between the chambers.

The vent passage of the analysis container 1 in this embodiment will be described.

Figure 9:
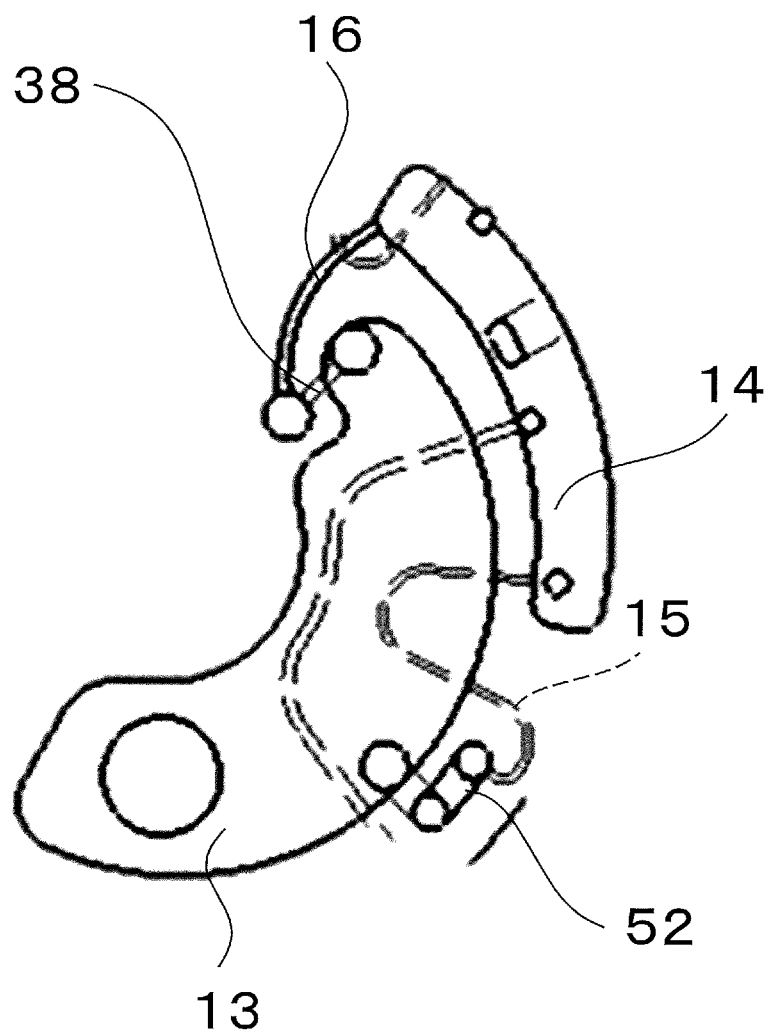
FIG. 9 is a top view of the main components of an analysis container depicting an embodiment of the present invention.

FIG. 9 shows the specimen extraction chamber 13 and the specimen quantification chamber 14 provided in the analysis container 1.

As discussed above, the specimen quantification chamber 14 is provided on the outer peripheral side of the specimen extraction chamber 13. The specimen extraction chamber 13 and the specimen quantification chamber 14 are connected by the liquid passage 15 and the vent passage 16. The specimen extract moves from the specimen extraction chamber 13 to the specimen quantification chamber 14 under the centrifugal force produced by rotating the analysis container 1 and the capillary force of the liquid passage 15 in the analysis container 1. At this point, air having a volume corresponding to the volume of the moved specimen extract moves from the specimen quantification chamber 14 to the specimen extraction chamber 13 via the vent passage 16.

That is, providing a passage for moving liquid between two chambers (the liquid passage 15) and a passage for moving air between two chambers (the vent passage 16) makes possible the movement of liquid even with a configuration without a vent hole in the sealed analysis container 1.

Description of Valve Mechanism of Vent Passage

Also, the vent passage 16 in this embodiment is provided with a valve mechanism 38 for accurately controlling the movement of liquid, rather than just allowing the movement of liquid between the chambers of the sealed analysis container 1.

As shown in FIG. 9, the valve mechanism 38, which controls the movement of air between the specimen extraction chamber 13 and the specimen quantification chamber 14, is provided on the specimen extraction chamber 13 side of the vent passage 16.

FIG. 10 and FIGS. 11A to 11D show the vent passage 16 and the valve mechanism of the vent passage 16.

In the passage configurations shown in FIG. 10 and FIGS. 11A to 11D, the characteristic portions of the actual passage configuration shown in FIG. 9 have been simplified to make them easier to understand.

Figure 10:
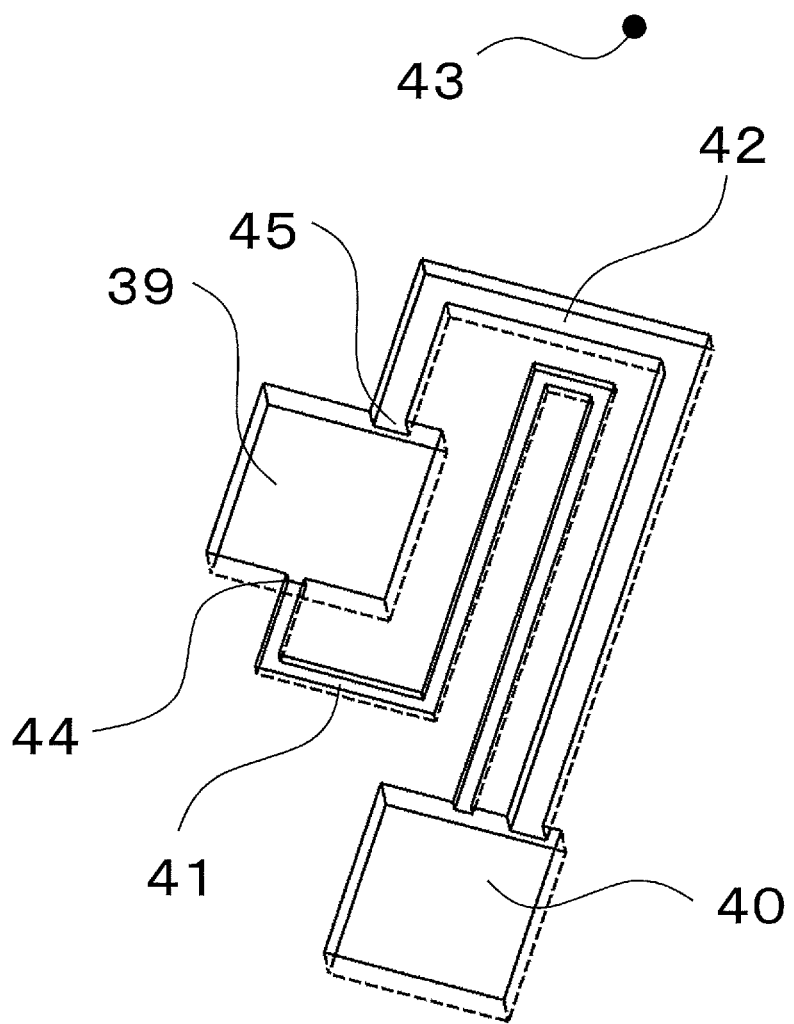
FIG. 10 is an oblique view of the main components of an analysis container depicting an embodiment of the present invention.

FIG. 10 is a simplified diagram illustrating the basic configuration of the vent passage 16 provided in the main body 1a of the analysis container 1.

More specifically, the analysis container 1 comprises a first chamber 39 (corresponds to the specimen extraction chamber 13) that is provided in the main body 1a and holds a liquid sample, a second chamber 40 (corresponds to the specimen quantification chamber 14), a liquid passage 41 that connects the first chamber 39 and the second chamber 40 and moves the liquid sample from the first chamber 39 to the second chamber 40, and a vent passage (air passage) 42 (corresponds to the vent passage 16) that connects the first chamber 39 and the second chamber 40 and moves air from the second chamber 40 to the first chamber 39.

This allows liquid to move from the first chamber 39 to the second chamber 40 even inside the sealed analysis container 1.

A rotational center 43 is provided in the approximate center (at the top in FIG. 10) in the main body 1a of the analysis container 1. The connection point 44 between the first chamber 39 and the liquid passage 41 is located farther from the rotational center 43 than the connection point of the first chamber 39 and the vent passage (air passage) 42.

Consequently, when centrifugal force is exerted on the analysis container 1 as it rotates around the rotational center 43, the liquid in the first chamber 39 moves in the outer peripheral direction and flows from the connection point 44 of the liquid passage 41 into the liquid passage 41.

Also, the liquid passage 41 is a capillary passage that moves liquid by capillary force. Therefore, the liquid sample that has flowed in from the connection point 44 moves through the liquid passage 41 under capillary force, and is stopped by surface tension ahead of the second chamber 40.

FIG. 11A to FIG. 11D show a valve mechanism 46 provided to the vent passage 42. The valve mechanism 46 stops the movement of air and thereby stops the movement of the liquid sample in the liquid passage 41.

FIGS. 11A to FIG. 11D show valve mechanisms 46a, 46b, 46c, and 46d with four different configurations, as other examples of the above-mentioned valve mechanism 46.

Figures 11A, 11B:
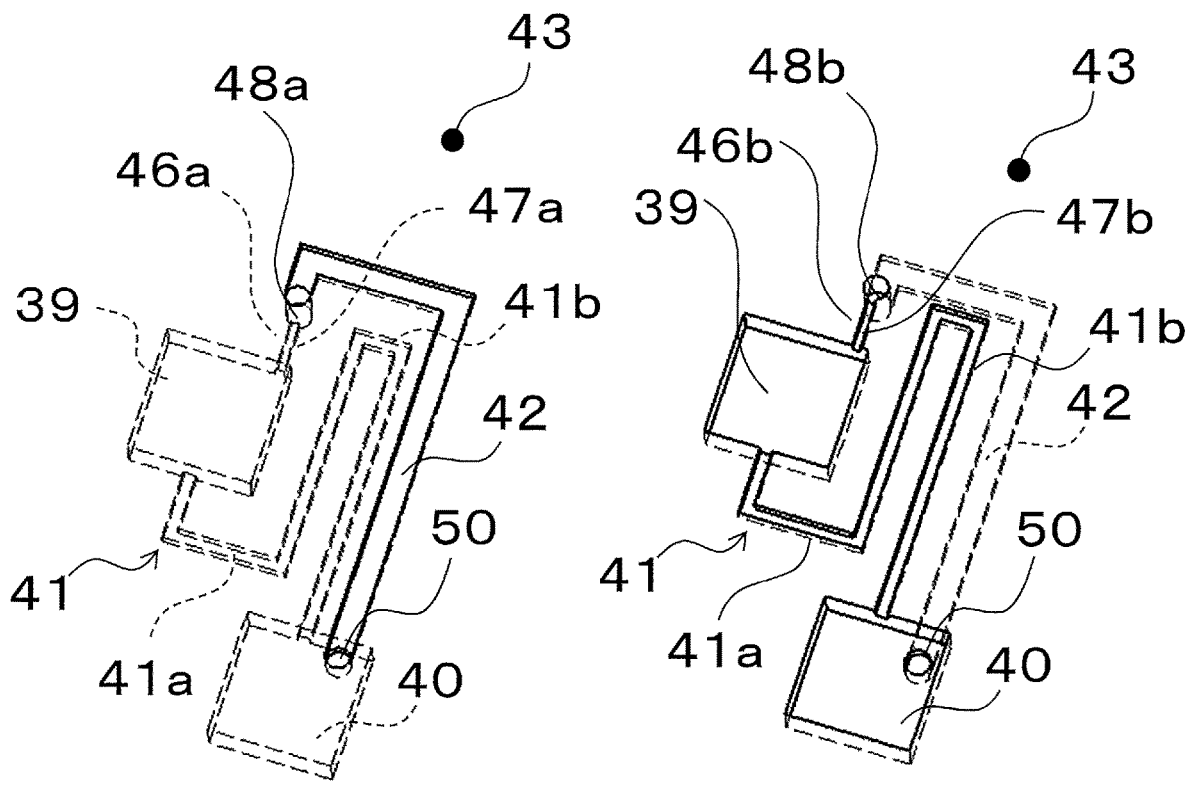
FIGS. 11A to 11D are oblique views of the main components of an analysis container depicting an embodiment of the present invention.

The valve mechanism 46a shown in FIG. 11A has a capillary passage 47a and a first passage 48a.

The capillary passage 47a is connected at a first end to the first chamber 39, extends toward the rotational center 43, and is connected to the first passage 48a at a second end on the opposite side from the first end. The first passage 48a extends upward in the vertical direction, and is connected to the vent passage 42.

The valve mechanism 46b shown in FIG. 11B has a capillary passage 47b and a first passage 48b.

The capillary passage 47b is connected at a first end to the first chamber 39, extends toward the rotational center 43, and is connected to the first passage 48b at a second end on the opposite side from the first end. The first passage 48b extends downward in the vertical direction, and is connected to the vent passage 42.

The first passages 48a and 48b have a substantially circular lateral cross sectional shape. The surface area of the lateral cross section is greater than that of the capillary passages 47a and 47b.

Consequently, there is no capillary action within the first passages 48a and 48b, so the liquid sample is not moved by capillary force.

The valve mechanisms 46a and 46b are used to stop the movement of air in the vent passage 42, but the movement of air in the vent passage 42 is stopped by introducing liquid into the capillary passages 47a and 47b to block off these capillary passages.

Figures 11C, 11D:
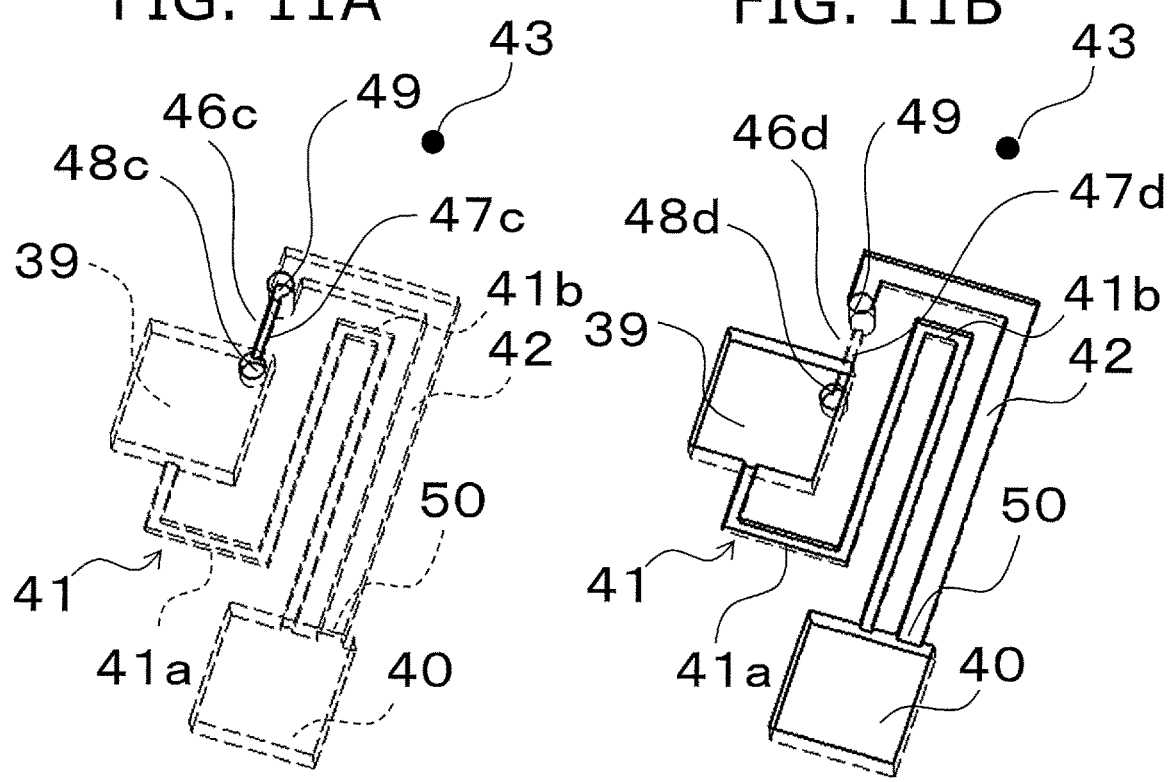

The valve mechanism 48c shown in FIG. 11C has a capillary passage 47c, a first passage 48c, and a second passage 49.

The first passage 48c is connected at a first end to the first chamber 39, extends upward in the vertical direction, and is connected to the capillary passage 47c at a second end on the opposite side. The capillary passage 47c extends toward the rotational center 43 and is connected to the second passage 49.

The second passage 49 extends downward in the vertical direction, and is connected to the vent passage 42.

As shown in FIG. 11D, the valve mechanism 46d has a capillary passage 47d, a first passage 48d, and the second passage 49.

The first passage 48d is connected at a first end to the first chamber 39, extends downward in the vertical direction, and is connected to the capillary passage 47d at a second end on the opposite side from the first end. The capillary passage 47d extends toward the rotational center 43, and is connected to the second passage 49. The second passage 49 extends upward in the vertical direction, and is connected to the vent passage 42.

The first passages 48c and 48d and the second passage 49 have a substantially circular lateral cross sectional shape. The surface area of this lateral cross section is greater than that of the capillary passage. Also, the lateral cross sectional shape of the first passages 48c and 48d and the second passage 49 is substantially circular. Consequently, there are no edges within the first passages 48c and 48d, so the liquid does not propagate. Because the surface area of the lateral cross section is sufficiently larger than the capillary passage, there is no propagation of the liquid due to surface tension in the first passages 48c and 48d or the second passage 49. That is, there is no capillary action within the first passages 48a and 48b or the second passage 49, so the liquid does not move.

The first passages 48a to 48d and the second passage 49 described in this embodiment are tubular passages extending in the vertical direction, and have a substantially circular lateral cross sectional shape. The surface area of this lateral cross section is sufficiently larger than that of the capillary passage 47.

Consequently, there is no propagation of the liquid due to surface tension. That is, there is no capillary action in the first passages 48a to 48d or the second passage 49, so the liquid sample does not move.

The valve mechanisms 46c and 46d control the movement of air in the vent passage 42. More specifically, liquid goes into the capillary passages 47c and 47d and blocks of these capillary passages, and this stops the movement of air in the vent passage 42.

Also, the capillary passages 47a, 47b, 47c, and 47d blocked off by the liquid extend toward the rotational center 43 from the connection with the first chamber 39. Therefore, when a centrifugal force that is stronger than the surface tension acting between the capillary passages and the first chamber 39 is exerted on the analysis container 1, the liquid in the capillary passages 47a, 47b, 47c, and 47d are returned by this centrifugal force to the first chamber 39 in the outer peripheral direction.

This allows the movement of air to resume in the vent passage 42.

FIGS. 12A to 12E show the movement of liquid in a passage configuration featuring the vent passage 42 and the valve mechanisms 46a to 46d.

The upper parts in FIGS. 12A to 12E are top views of the passage configuration, and the lower parts are cross sections along the A-A' line in the top views.

In FIG. 12A, the analysis container 1 in FIG. 12B is rotated from a stationary state to exert centrifugal force (see the arrow in the drawing), and in this state, the liquid sample is drawn from the connection point 44 of the liquid passage 41 into the liquid passage 41, and then moves through the liquid passage 41.

The liquid passage 41, as viewed from the rotational center 43, extends outward in the radial direction from the first chamber 39, and after passing through a valley portion 41a that is bent outward radially, extends back toward the rotational center side. The liquid passage 41 has a peak portion 41b that bends to the rotational center side, and has a siphon shape that connects to the second chamber 40.

In the state in FIG. 12B in which centrifugal force is exerted, the liquid moves in the radial direction around the rotational center, to a position at substantially the same liquid level in the first chamber 39 from the valley portion 41a of the liquid passage 41 to the peak portion 41b, and comes to a stop.

As shown in the lower cross section in FIG. 12B, at this point the liquid sample has not yet entered the valve mechanism 46.

After this, as shown in FIG. 12C, the centrifugal force is eliminated when the rotation is suddenly stopped, so the liquid moves to the connection point 50 between the second chamber 40 and the liquid passage 41, and comes to a stop. At the same time, the sudden stop of the rotation causes the liquid in the first chamber 39 to splash up against a first wall 80 that is perpendicular to the rotation direction (the right side in the drawing).

The connection point 51 between the first chamber 39 and the vent passage 42 is provided near the corner on the inner peripheral side of the first wall 80. Therefore, the liquid that hits the first wall 80 goes from the connection point 51 into the valve mechanism 46 of the vent passage 42.

As a result, the liquid goes from the connection point 51 between the first chamber 39 and the vent passage 42 into the capillary passage of the valve mechanisms 46a to 46d, and fills the capillary passage by capillary action, which stops the movement of air in the vent passage 42.

Here, as shown in the cross section in the lower part of FIG. 12C, the first passages 48a and 48b and the second passage 49 connected to the capillary passages of the valve mechanisms 46a to 46d are not capillary passages. Thus, the liquid is not drawn into these passages that are not subjected to capillary force.

As shown in FIGS. 11C and 11D, the valve mechanisms 46c and 46d of the vent passage 42 are such that the capillary passages 47c and 47d and the first chamber 39 are connected via the first passages 48c and 48d. Accordingly, compared to the valve mechanisms 46a and 46b in FIGS. 11A and 11B, the liquid in the first chamber 39 is less likely to enter the capillary passages 47c and 47d.

In such a case, the stirring shown in FIG. 12D is performed so that the liquid will reliably go through the first passages 48c and 48d and enter the capillary passages 47c and 47d connected to the first chamber 39.

This stirring operation is performed by a rocking motion in which the analysis container 1 is alternately rotated forward and backward. This allows the liquid to reliably go through the first passages 48c and 48d and enter the capillary passages 47c and 47d connected to the first chamber 39.

This stirring operation is required in order to stir the liquid in the first chamber 39. However, since this rocking motion is subjected to centrifugal force as an external disturbance, in FIG. 11C, there is the risk that the liquid stopped at the connection point 50 between the liquid passage 41 and the second chamber 40 will end up entering the second chamber 40 by mistake.

With the analysis container 1 in this embodiment, even is centrifugal force is produced by a shaking operation, the liquid in the first chamber 39 is stirred while the valve mechanisms 46c and 46d of the vent passage 42 are simultaneously closed to stop the movement of air. This prevents the liquid that is stopped at the connection point 50 from accidentally entering the second chamber 40, while enabling a more stable stirring operation.

After the stirring operation in FIG. 12D is complete, as shown in FIG. 12E, the analysis container 1 is rotated again to generate centrifugal force (the arrow in the drawing). The capillary passages 47a, 47b, 47c, and 47d that are blocked off by the liquid extend toward the rotational center 43 with respect to the first chamber 39. Therefore, when the analysis container 1 is subjected to centrifugal force, the liquid in the capillary passages 47a, 47b, 47c, and 47d is moved by centrifugal force and goes back to the first chamber 39 in the outer peripheral direction. Consequently, the movement of the air in the vent passage 42 is restored.

The liquid stopped at the connection point 50 between the liquid passage 41 and the second chamber 40 can then be reliably moved into the second chamber 40 by centrifugal force and by the movement of air produced by the vent passage 42.

In the above configuration, a configuration was described in which the first chamber 39 and the second chamber 40 were connected by the vent passage 42.

Figure 13A:
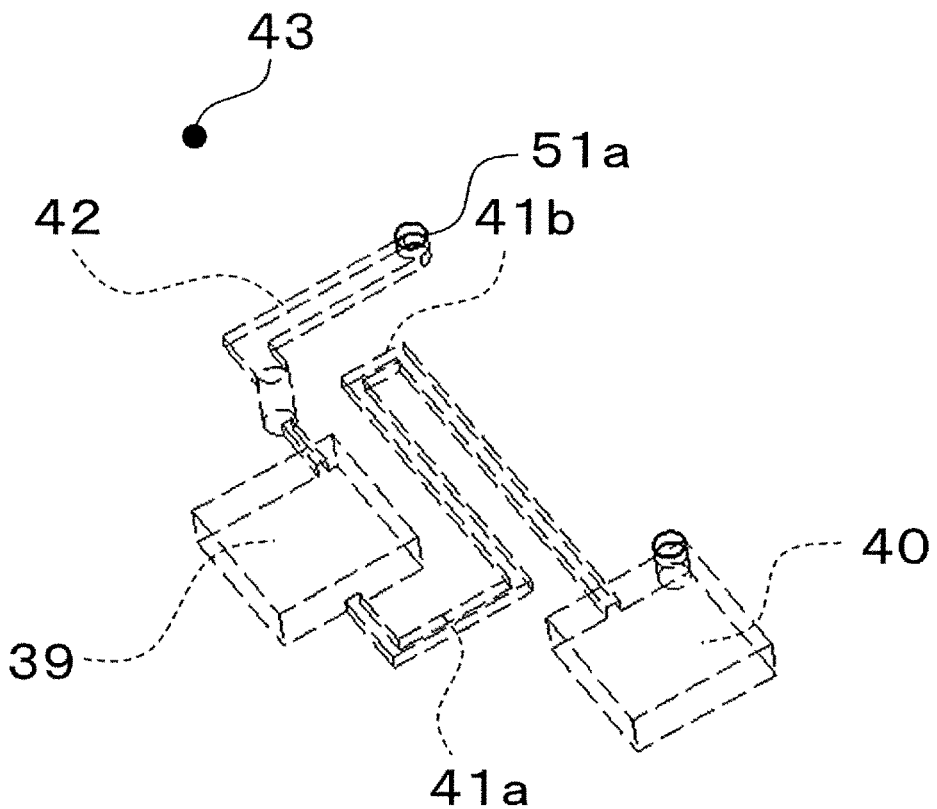
FIGS. 13A and 13B are oblique views of the main components of an analysis container depicting an embodiment of the present invention.
Figure 13B:
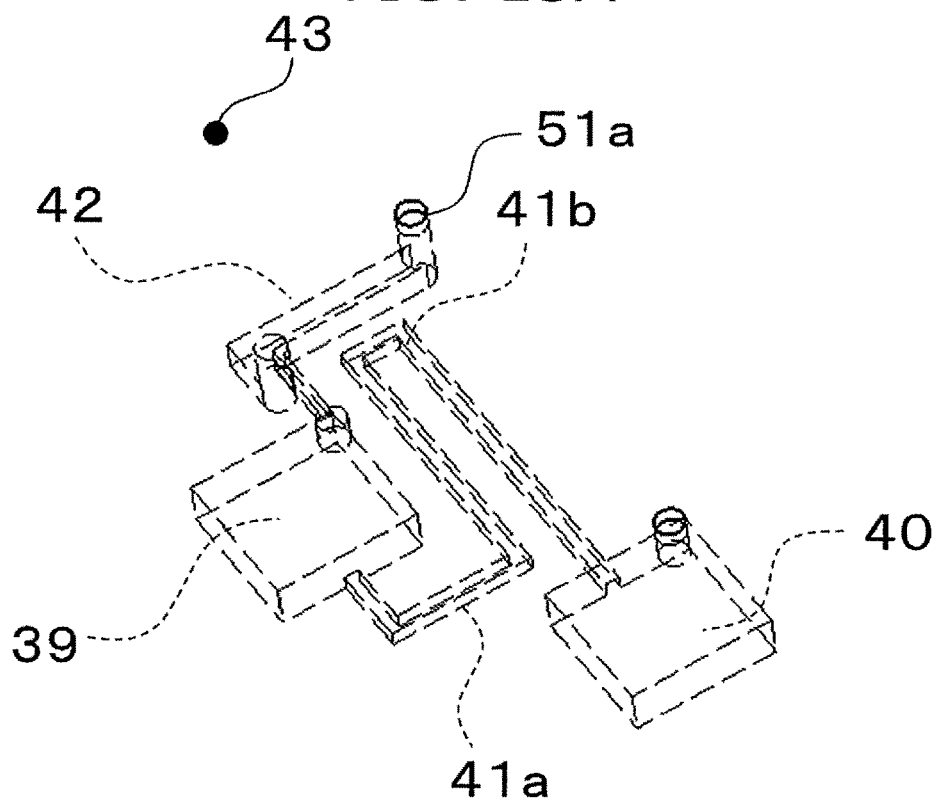

However, as shown in FIGS. 13A and 13B, the configuration may also be such that the second end of the vent passage 42 connected to the first chamber 39 communicates with an opening 51a provided to the surface of the main body 1a of the analysis container 1. In this configuration, the analysis container 1 is open rather than sealed, that is, it is an outside air circulation type, so outside air can be brought in.

As described above, the analysis container 1 in this embodiment comprises the main body 1a, the first chamber 39 that is provided to the main body 1a and holds a liquid sample, the second chamber 40, the liquid passage 41 that connects the first chamber 39 and the second chamber 40 and moves the air in the first chamber 39, and the vent passage 42 that moves is connected to the first chamber 39 and moves the air in the first chamber 39. The valve mechanisms 46a to 46d that control the movement of air are provided to the vent passage 42

Consequently, the liquid specimen in the sealed analyzed container 1 can be accurately moved between chambers.

That is, with the analysis container 1 in this embodiment, if the liquid specimen is to be kept in the first chamber 39, such as when the liquid in the first chamber 39 is stirred, the valve mechanisms 46a to 46d of the vent passage 42 are put in their closed state.

Consequently, no air will go into the first chamber 39 from the vent passage 42, so the negative pressure generated in the first chamber 39 will create a state in which the liquid specimen is less likely to come out of the first chamber 39, and the liquid specimen can be kept inside. As a result, the liquid specimen in the analysis container 1 can be accurately moved between chambers.

Description of Valve Mechanisms of Liquid Passages

The valve mechanisms of the liquid passages will now be described.

Returning to FIG. 9, the valve mechanism 52 of the liquid passage 15 will be described.

As shown in FIG. 9, the valve mechanism 52 for controlling movement of the liquid sample in the liquid passage 15 is provided on the sample extraction chamber 13 side of the liquid passage 15.

Figure 14A:
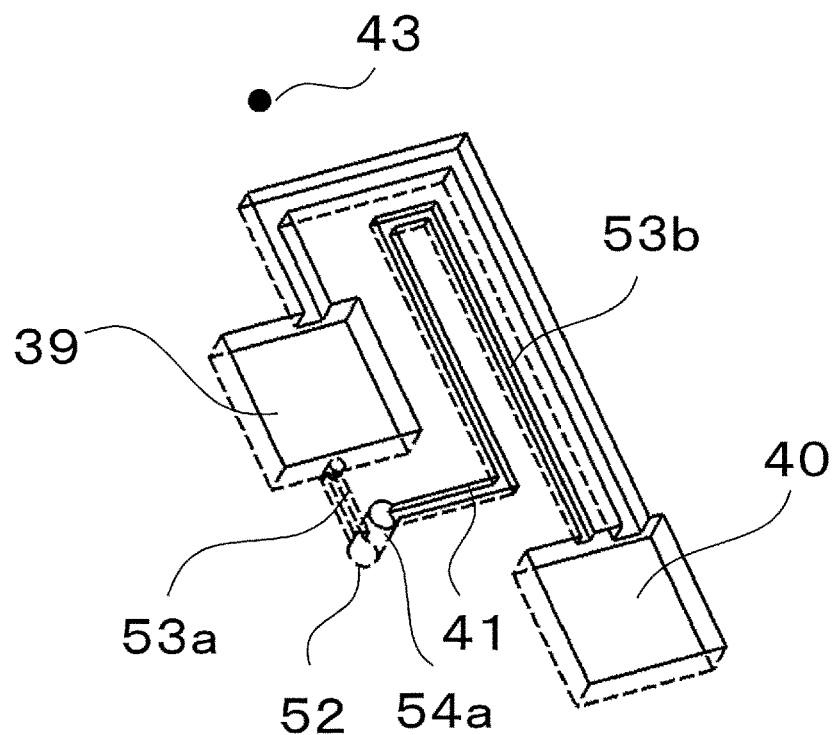
FIGS. 14A and 14B are oblique views of the main components of an analysis container depicting an embodiment of the present invention.
Figure 14B:
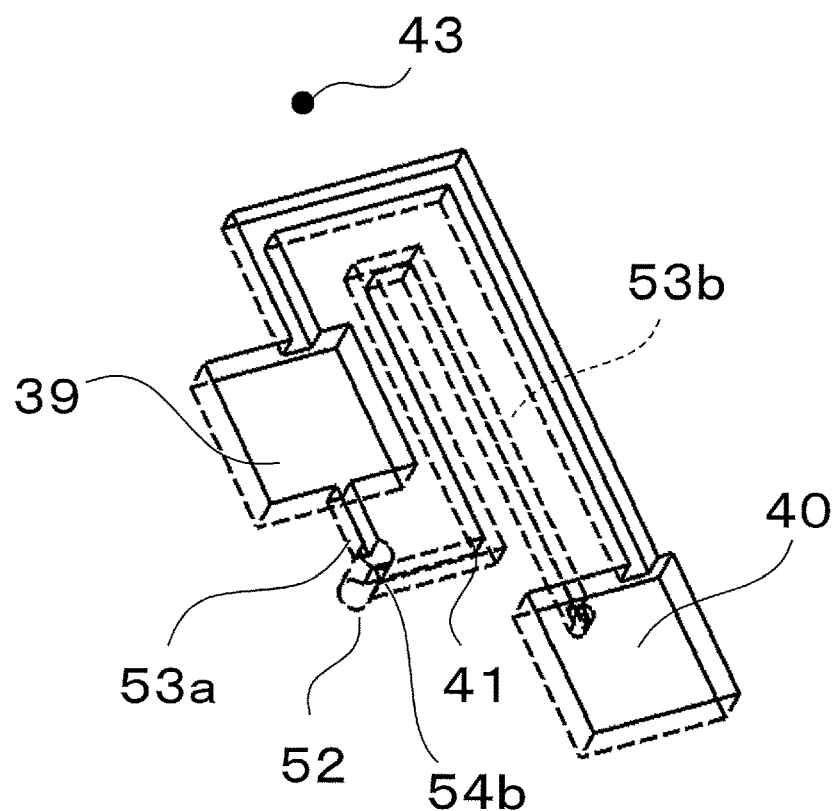

FIGS. 14A and 14B show the valve mechanism 52 of the liquid passage 41 (corresponds to the liquid passage 15).

In the passage configuration shown in FIGS. 14A and 14B, the characteristic portion of the actual passage configuration shown in FIG. 9 has been simplified to make it easier to understand.

FIGS. 14A and 14B are simplified views of the basic configuration of the valve mechanism 52 of the liquid passage 15 provided in the main body 1a of the analysis container 1.

As shown in FIG. 14A, the analysis container 1 is provided with the main body 1a and the first chamber 39 (corresponds to the sample extraction chamber 13) and the second chamber 40 (corresponds to the sample quantitative chamber 14) that are provided in the main body 1a and hold the liquid sample. Furthermore, the analysis container 1 is provided with the first liquid passage 41 (corresponds to the liquid passage 15), which connects the first chamber 39 and the second chamber 40 and moves the liquid sample from the chamber 39 to the second chamber 40.

The valve mechanism 52 for adjusting the movement of the liquid sample in the liquid passage 41 is provided to the liquid passage 41.

The liquid passage 41 has a lead-out passage 53a that is connected to the first chamber 39, and a lead-in passage 53b that is connected to the second chamber 40.

The valve mechanism 52 is linked to the lead-out passage 53a. The valve mechanism 52 has the first passage 54a that extends vertically upward as shown in FIG. 14A, or the first passage 54b that extends vertically downward as shown in FIG. 14B.

The lead-out passage 53a is constituted by a capillary passage for moving the liquid sample by capillary force. The lead-in passage 53b from the valve mechanism 52 to the second chamber 40 is also constructed by a capillary passage.

The lead-out passage 53a is connected at a first end to the first chamber 39, extends away from the rotational center 43 from the first end, and is connected to the first passages 54a and 54b at a second end that is on the opposite side from the first end.

The first passages 54a and 54b have a substantially circular lateral cross sectional shape, in which the surface area of a lateral cross section perpendicular to the longitudinal direction is larger than that of the lead-out passage 53a or the lead-in passage 53b, which are capillary passages.

Because the first passages 54a and 54b have a substantially circular cross sectional shape, in addition to the fact that the surface area of a lateral cross section is larger than that of the lead-out passage 53a or the lead-in passage 53b, which are capillary passages, no capillary force is exerted on the liquid in the interior.

Figure 15A:
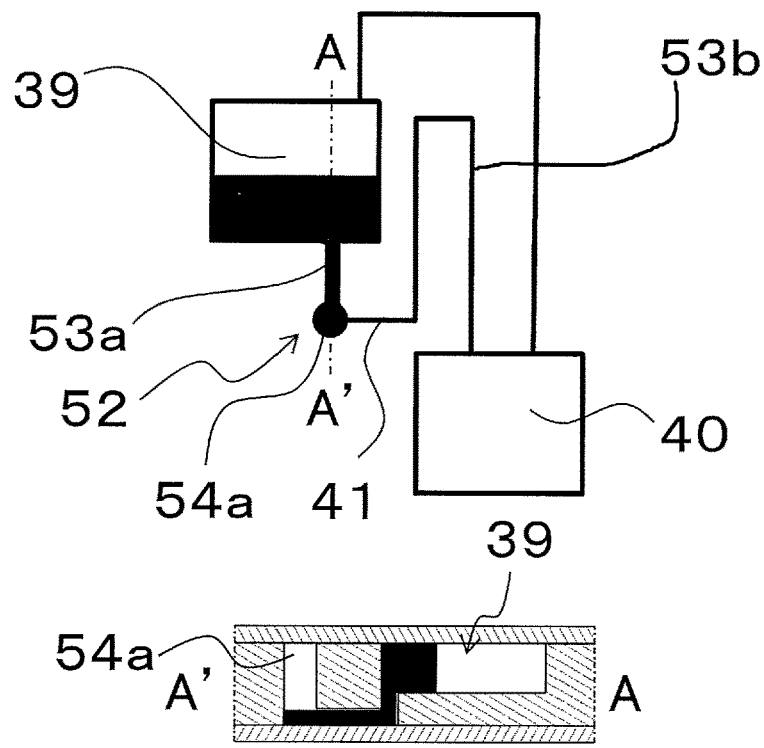
FIGS. 15A and 15B show top views of the main components of an analysis container depicting an embodiment of the present invention in the upper parts.
Figure 15B:
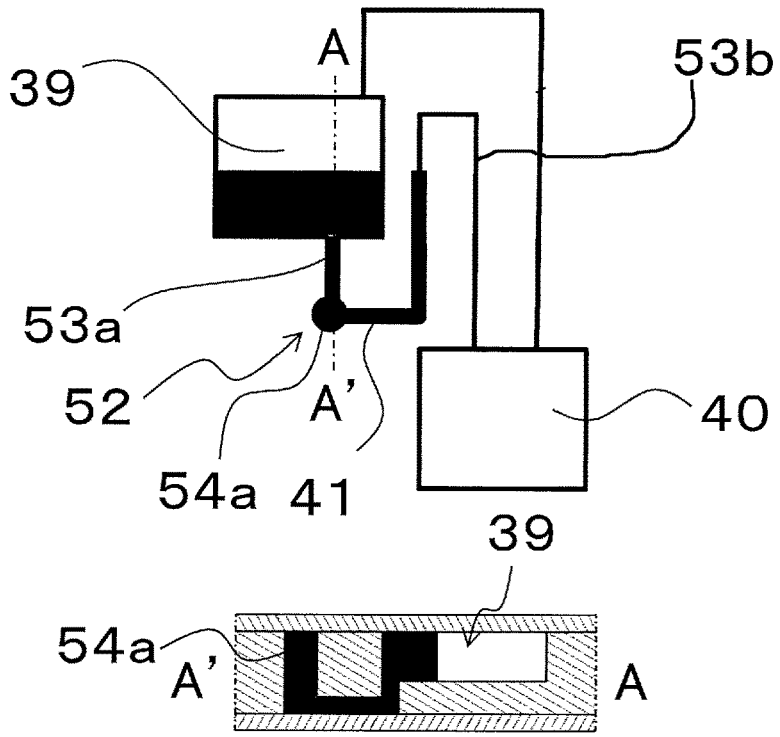

FIGS. 15A and 15B shows the flow of the liquid sample using the valve mechanism 52.

FIG. 15A shows a stationary state in which no centrifugal force is acting on the analysis container 1. In this state, the liquid sample in the first chamber 39 flows under the capillary force of the lead-out passage 53a, stops ahead of the first passage 54a. This is because no capillary force is acting on the first passage 54a.

Then, as shown in FIG. 15B, when the analysis container 1 is rotated, centrifugal force is exerted on the liquid sample in the first chamber 39 and the lead-out passage 53a.

Consequently, the liquid sample passes through the first passage 54a, moves through the lead-in passage 53b, and moves to position of equilibrium with the centrifugal force, that is, a position at substantially the same liquid level as the liquid sample in the first chamber 39 in the radial direction of a circle whose center is the rotational center. When the rotation of the analysis container 1 then comes to a stop, the liquid sample moves under the capillary force of the lead-in passage 53b to ahead of the second chamber 40, and its surface tension brings it to a halt. Then, when the analysis container 1 is rotated again, the liquid sample starts going into the second chamber 40 under centrifugal force.

Here, in the configuration had no valve mechanism 52, there would be a risk that the liquid sample would go from its stationary state and move all at once to a position ahead of the second chamber 40 under the capillary force of the liquid passage 41, so the movement of the liquid sample could not be controlled in steps.

Because the analysis container 1 in this embodiment comprises the valve mechanism 52, as described above, the liquid sample can be controlled in four stages of stationary, rotating, stationary, and rotating. As a result, the flow of the liquid sample from the first chamber 39 to the second chamber 40 can be accurately controlled.

That is, with the analysis container 1 in this embodiment, when the liquid sample is sent from the first chamber 39, through the liquid passage 41, to the second chamber 40, regardless of the size of the capillary force of the liquid sample in the passage, in the first passage 54a provided to the valve mechanism 52 of the passage, surface tension alone will be inadequate to make the liquid sample rise to the height generated in the first passage 54a, or to descend to the height of the first passage 54b.

This allows the liquid sample to be held below the first passage 54a or above the first passage 54b. Therefore, it is possible to reliably keep the liquid sample in this position.

When the analysis container 1 is rotated from this state, centrifugal force is exerted on the liquid sample in the first chamber 39 and in the lead-out passage 53a.

At this point, centrifugal force is exerted radially outward on the liquid sample in the first chamber 39 and the liquid sample in the lead-out passage 53a. Then, while being pushed by this centrifugal force, the liquid sample in the lead-out passage 53a moves radially outward and flows into the first passage 54a, and is pushed against the surface on the outside in the radial direction and moves through the first passage 54a.

Consequently, the liquid sample goes up in the vertical direction as far as possible through the first passage 54a, or goes down in the vertical direction as far as possible through the first passage 54b. The liquid sample then moves through the lead-in passage 53b under capillary force and centrifugal force to the second chamber 40. As a result, the liquid sample in the analysis container 1 can be moved accurately between chambers.

Description of Quantitative Chambers

The quantitative chambers will now be described.

Returning to FIG. 4, the dispensing chamber 27 and the quantitative chambers 28a, 28b, and 28c will be described.

As discussed above, the liquid mixture that was mixed in the mixing chamber 19 goes through the capillary passage 76 and enters the dispensing chamber 27. The mixture dispensed from the dispensing chamber 27 is quantified into the quantitative chambers 28a, 28b, and 28c.

When quantifying from the dispensing chamber 27 to the quantitative chambers 28a, 28b, and 28c, the analysis container 1 is in a state of rotating at high speed. Therefore, the centrifugal force causes the liquid sample to be quantified in stages to the quantitative chamber 28a, the quantitative chamber 28b, and the quantitative chamber 28c, in that order.

The dispensing chamber 27 is formed in an arc shape with respect to the rotational center (the rotary shaft insertion hole 12). The quantitative chambers 28a, 28b, and 28c extend in a comb shape toward the outer peripheral side in the radial direction. That is, the quantitative chambers 28a, 28b, and 28c are disposed on substantially the same circumference with respect to the rotational center (the rotary shaft insertion hole 12).

Figure 16:
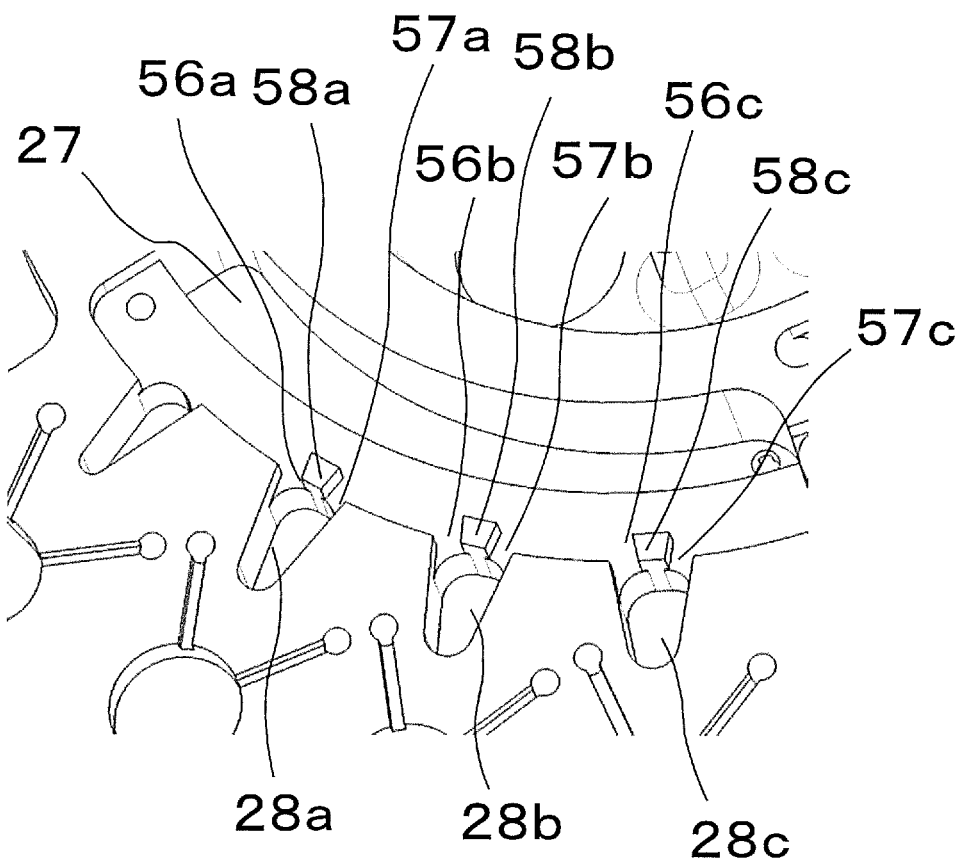
FIG. 16 is an oblique view of the main components of an analysis container depicting an embodiment of the present invention.

FIG. 16 is an oblique view of the configuration of the dispensing chamber 27 and the quantitative chambers 28a, 28b, and 28c.

The respective connecting portions between the dispensing chamber 27 and the quantitative chambers 28a, 28b, and 28c are provided with inlets 56a, 56b, and 56c for allowing the liquid to flow into the quantitative chambers 28a, 28b, and 28c, and outlets 57a, 57b, and 57c for allowing the liquid to flow out of the quantitative chambers 28a, 28b, and 28c.

These inlets 56a, 56b, and 56c and outlets 57a, 57b, and 57c are provided at both ends of partition walls 58a, 58b, and 58c provided to the connecting portions. The inlets 56a, 56b, and 56c and outlets 57a, 57b, and 57c provided to both ends of the partition walls 58a, 58b, and 58c are disposed on substantially the same circumference centered on the rotational center.

Figure 17A:
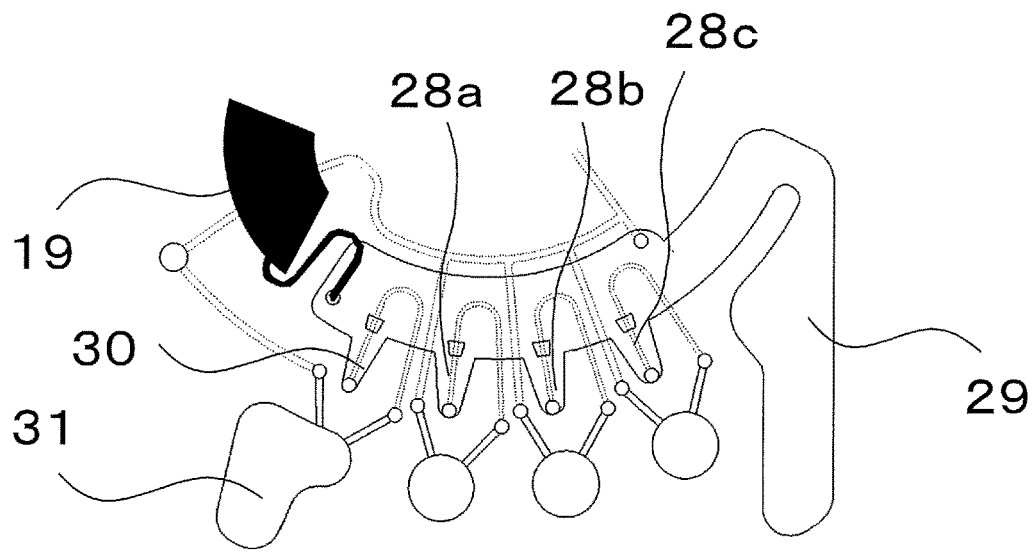
FIGS. 17A to 17C are top views of the main components of an analysis container depicting an embodiment of the present invention.
Figure 17B:
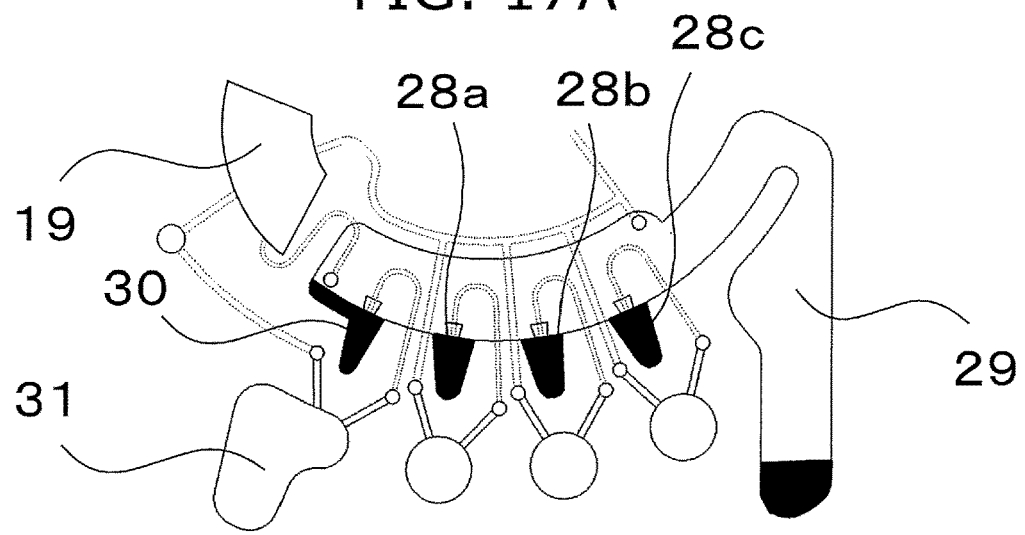
Figure 17C:
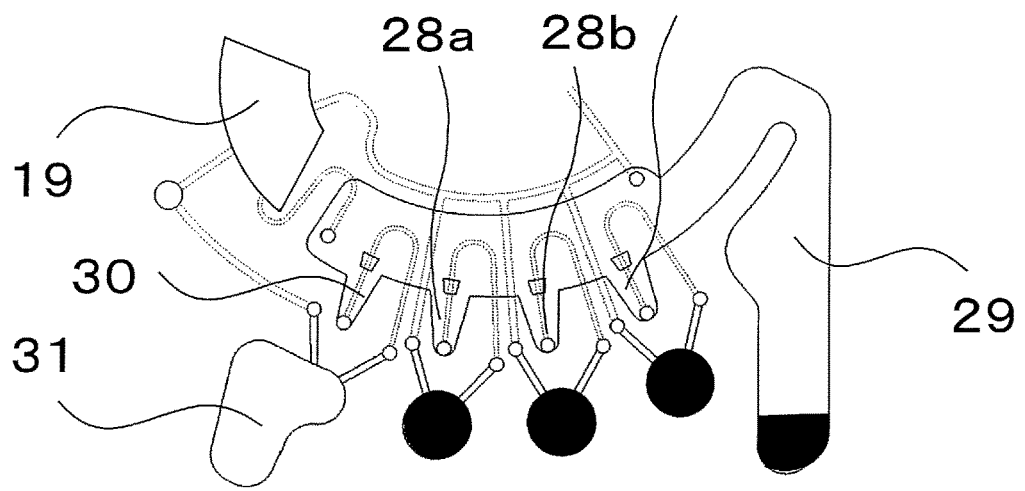

FIGS. 17A to 17C show the process of quantifying the liquid sample in the quantitative chambers 28a, 28b, and 28c.

In FIG. 17A, the inlets 56a, 56b, and 56c and the outlets 57a, 57b, and 57c are formed so that their opening area is large enough to produce surface tension. When the liquid sample that has moved to the quantitative chambers 28a, 28b, and 28c is quantified from the dispensing chamber 27, the liquid sample first flows from the inlet 56a into the quantitative chamber 28a.

At this time, the centrifugal force generated by the rotation of the analysis container 1 causes the liquid sample to be subjected to a force (centrifugal force) stronger than the surface tension produced in the inlet 56a and flow into the quantitative chamber 28a. Upon going past the quantitative chamber 28a and overflowing, the liquid sample flows out of the outlet 57a and then flows into the next quantitative chambers 28b and 28c, in that order.

Then, in FIG. 17B, once the quantitative chambers 28a, 28b, and 28c have been filled with the liquid sample, the rotation of the analysis container 1 is stopped, creating a state in which no centrifugal force is exerted on the liquid sample. At this point, in a state in which the rotation of the analysis container 1 is stopped, the inlets 56a, 56b, and 56c and the outlets 57a, 57b, and 57c function as surface tension valves that hold the liquid sample in the quantitative chambers 28a, 28b, and 28c with the surface tension acting on the liquid sample.

Therefore, the liquid sample is in a state in which it cannot flow in or out of the quantitative chambers 28a, 28b, and 28c. This prevents external disturbance such as gravity from causing the liquid sample in the quantitative chambers 28a, 28b, and 28c to flow out to the other quantitative chambers 28a, 28b, and 28c.

Consequently, there is less variance in the amounts of specimen held in the quantitative chambers 28a, 28b, and 28c. As a result, the proper analysis can be carried out.

In this embodiment, two more chambers are provided for quantifying. The first chamber is the overflow chamber 29 that holds any surplus liquid mixture. The second chamber is the trap chamber 30.

That is, the mixture remaining in the mixing chamber 19 ends up flowing into the quantitative chambers 28a, 28b, and 28c after quantifying in the quantitative chambers 28a, 28b, and 28c. When this happens, it may impair quantifying in the quantitative chambers 28a, 28b, and 28c, making it more difficult to conduct the subsequent reaction accurately.

In view of this, as shown in FIGS. 17A to 17C, the analysis container 1 in this embodiment comprises the trap chamber 30, which is provided on the upstream side of the quantitative chambers 28a, 28b, and 28c, and the reservoir 31, which is connected to the trap chamber 30 via a passage.

This allows the reaction to be carried out accurately without the quantifying in the quantitative chambers 28a, 28b, and 28c being impaired by the mixture remaining in the mixing chamber 19.

Description of Synchronization Passage

A synchronization passage will now be described.

Figure 18:
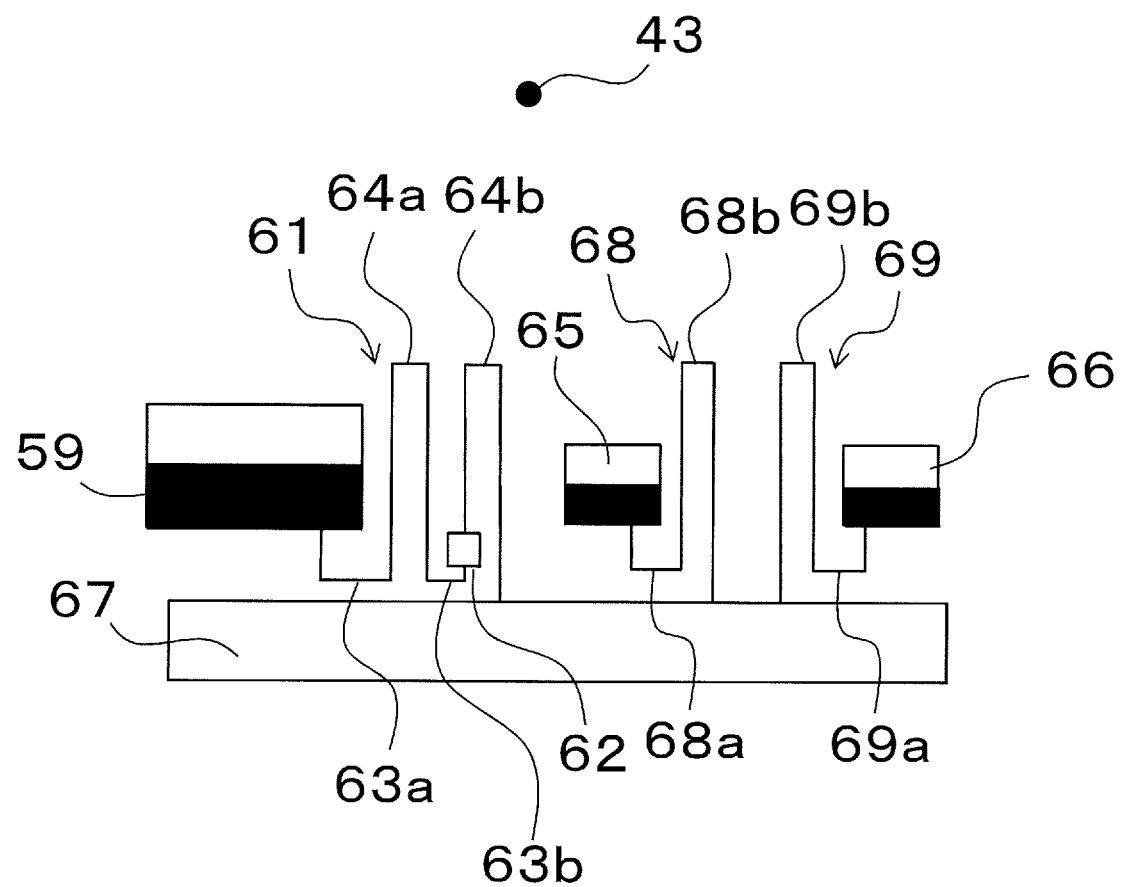
FIG. 18 is a top view of the main components of an analysis container depicting an embodiment of the present invention.

FIG. 18 shows the configuration of the synchronization passage.

The synchronization passage comprises a first chamber 59 for holding a liquid sample, a liquid passage 61, a valve mechanism 62, and the rotational center 43 of the analysis container 1.

The liquid passage 61 connects a mixing chamber 67 and the first chamber 59, and moves the liquid sample from the first chamber 59 to the mixing chamber 67.

Also, the liquid passage 61 is configured to combine a plurality of siphon-shaped passages including a valley portion 63a that protrudes radially outward (as viewed from the rotational center 43) from the connection portion with the first chamber 59, and a peak portion 64a that passes through the valley portion 63a and then protrudes back toward the rotational center 43 side.

The valve mechanism 62 is provided at a position between a valley portion 63b and a peak portion 64b along the liquid passage 61. That is, as shown in FIG. 18, the valve mechanism 62 is provided to the liquid passage 61 at a position that is past the first valley portion 63a and the first peak portion 64a, and is past the second valley portion 63b protruding back toward the outside in the radial direction, but is before the second peak portion 64b protruding toward the rotational center 43 side.

The valve mechanism 62 is provided along the liquid passage 61, and adjusts the movement of the liquid sample in the liquid passage 61. As shown in FIG. 18, the valve mechanism 62, as seen from the rotational center 43, is provided at a position farther away in the radial direction than the first chamber 59.

The valley portions 63a and 63b of the liquid passage 61, as viewed from the rotational center 43, are provided at positions farther away in the radial direction than the first chamber 59. The peak portions 64a and 64b of the liquid passage 61, as viewed from the rotational center 43, are provided at positions closer in the radial direction than the first chamber 59.

More specifically, the valley portions 63a and 63b and the peak portions 64a and 64b are provided at the height of the liquid level when the liquid sample has been moved radially outward by the centrifugal force generated by rotation of the analysis container 1.

That is, the valley portions 63a and 63b of the liquid passage 61, as viewed from the rotational center 43, are provided at positions farther away in the radial direction than the height of the liquid level of the first chamber 59. Also, the peak portions 64a and 64b of the liquid passage 61, as viewed from the rotational center 43, are provided at positions closer in the radial direction than the height of the liquid level of the first chamber 59.

FIGS. 19A to 19F show the steps of synchronization in the synchronization passage.

The synchronization passage shown in FIG. 19A to FIG. 19F, in addition to the configuration of the synchronization passage illustrated in FIG. 18, further comprises a third chamber 65, a fourth chamber 66, a mixing chamber 67, a siphon passage 68, and a siphon passage 69.

The third chamber 65 and fourth chamber 66 store a liquid sample.

The siphon passage 68 connects the mixing chamber 67 and third chamber 65.

The siphon passage 69 connects the mixing chamber 67 and fourth chamber 66.

Figure 19A:
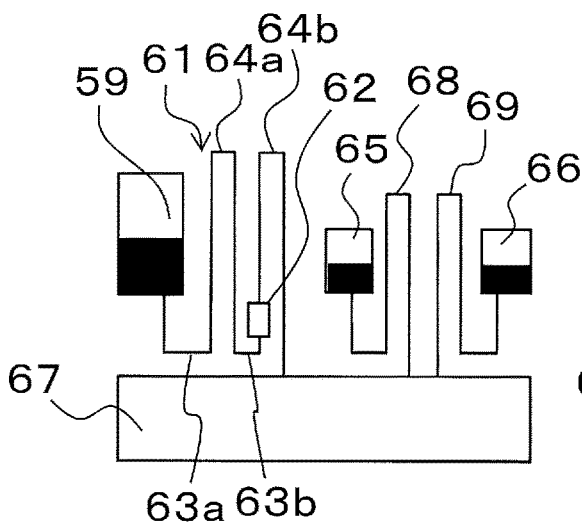
FIGS. 19A to 19F are top views of the main components of an analysis container depicting an embodiment of the present invention.

FIG. 19A shows the state when the rotation of the analysis container 1 has stopped.

At this point, the first chamber 59, the third chamber 65, and the fourth chamber 66 each hold a liquid sample.

Figure 19B:
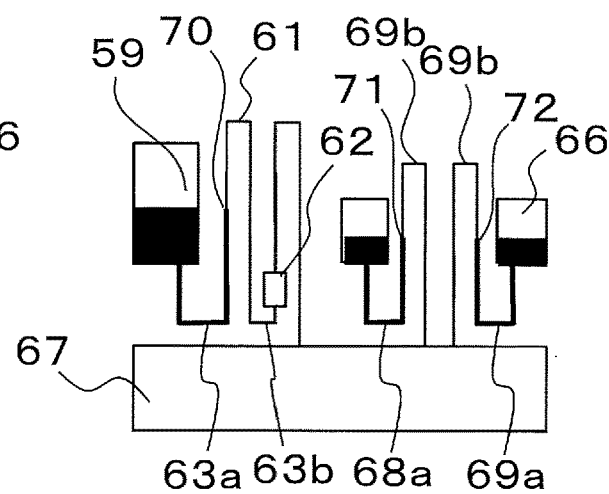

Next, FIG. 19B shows the state when the analysis container 1 is rotating at a high speed.

At this point, the liquid samples in the first chamber 59, the third chamber 65, and the fourth chamber 66 move through the liquid passage 61 and the siphon passages 68 and 69. The liquid samples then stop at the point where equilibrium is reached between the centrifugal force and the capillary force in liquid passage 61, that is, the position where the liquid sample in the first chamber 59 is subjected to centrifugal force and is located in the radial direction at the same height as the liquid level after moving outward in the radial direction.

The liquid sample in the first chamber 59 moves through the liquid passage 61 and stops at the point 70 between the valley portion 63a and the peak portion 64a.

The liquid sample in the third chamber 65 moves through the siphon passage 68 and stops at the point 71 between the valley portion 68a and the peak portion 68b.

The liquid sample in the fourth chamber 66 moves through the siphon passage 69 and stops at the point 72 between the valley portion 69a and the peak portion 69b.

Figure 19C:
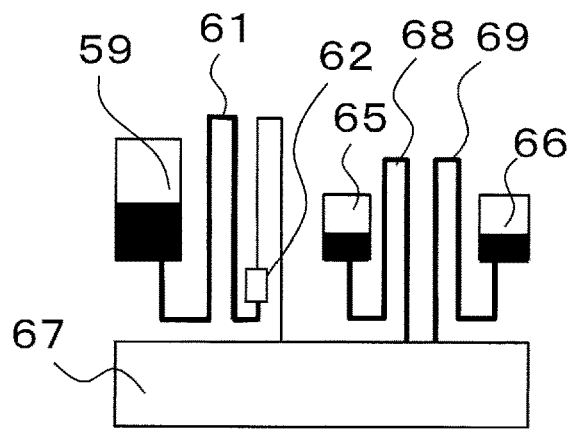

Next. FIG. 19C shows the state when the rotation of the analysis container 1 is stopped again.

At this point the centrifugal force goes away, so the liquid sample in the liquid passage 61 is moved by capillary force. The liquid sample then moves through the siphon passages 68 and 69 to the connection point with the mixing chamber 67, where it is stopped by surface tension. The liquid sample in the liquid passage 61 then moves to the connection point with the valve mechanism 62, where it is stopped by surface tension.

Figure 19D:
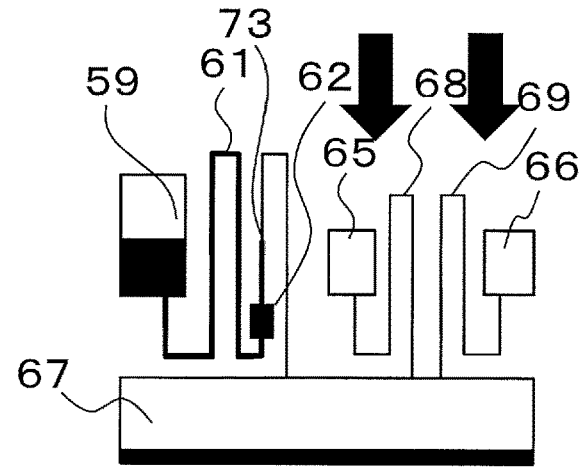

Next, FIG. 19D shows the state when the analysis container 1 is rotating at high speed again.

At this point the liquid sample in the siphon passages 68 and 69 that has been stopped by surface tension at the connection point with the mixing chamber 67, flows into the mixing chamber 67 under centrifugal force acting in the direction of the arrow in the drawing, where it is mixed with the other liquid samples. The liquid sample in the liquid passage 61 that has been stopped by surface tension at the connection point with the valve mechanism 62 then passes the valve mechanism 62 under centrifugal force, and stops at the point 73 where the capillary force and the centrifugal force of the liquid passage are at equilibrium.

Figure 19E:
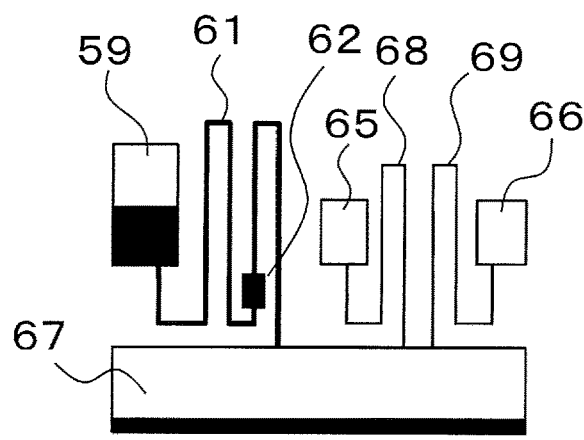

Next, FIG. 19E shows the state when the rotation of the analysis container 1 is stopped again.

At this point the liquid sample in the liquid passage 61 is not subjected to any centrifugal force, so it is moved by capillary force, and the liquid sample in the liquid passage 61 moves to the connection point with the mixing chamber 67, where it is stopped by surface tension.

Figure 19F:
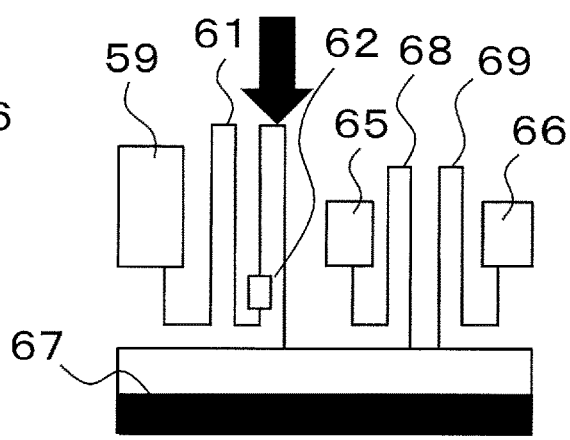

Next, FIG. 19F shows the state when the analysis container 1 is rotating at a high speed again.

At this point the liquid sample in the liquid passage 61 that has been stopped by surface tension at the connection point with the mixing chamber 67 enters the mixing chamber 67 under centrifugal force, where it mixes with the other liquid samples.

In the passage configuration described above, performing the above steps allows the liquid sample in the first chamber 59 to be moved into the mixing chamber 67 after the liquid samples held in the third chamber 65 and the fourth chamber 66 have been mixed in the mixing chamber 67.

Consequently, after the liquid samples held in the third and fourth chambers have been mixed in the mixing chamber 67, the liquid sample in the first chamber 59 is moved into the mixing chamber 67, which makes it possible to mix the liquid samples in stages.

For example, a liquid sample containing specimen cells is put into the third chamber 65, a cell wall lysis solution is put into the fourth chamber 66, and a marker reagent for recognizing a particular gene in a cell is put into the first chamber 59.

In this case, first, the liquid containing the specimen cells and the cell wall lysis solution are moved into the mixing chamber 67 and mixed. Then, the marker reagent is moved into the mixing chamber 67 and mixed with the mixture of the liquid containing the specimen cells and the cell wall lysis solution.

Consequently, after the cell walls of the specimen cells have been dissolved and just the gene portion of the cells has been taken out, the marker reagent that recognizes those genes can be mixed in to confirm whether or not a particular gene is present.

FIGS. 20A and 20B, FIGS. 21A and 21B, and FIGS. 22A and 22B show the configuration of three types of the valve mechanism 62.

Figure 20A:
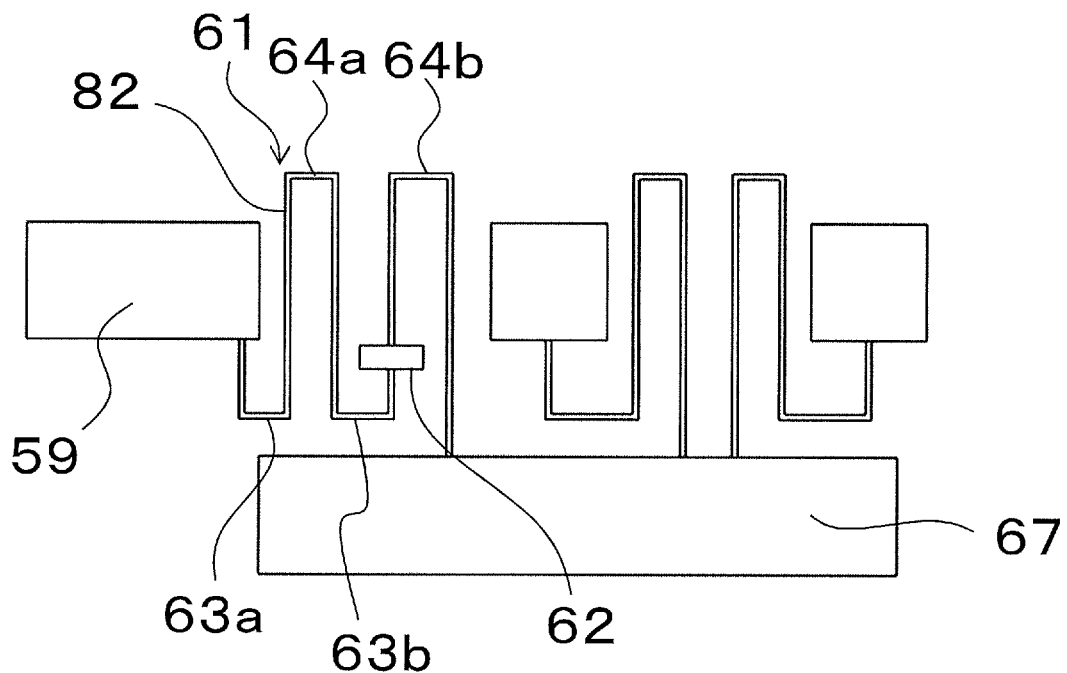
FIGS. 20A and 20B are a top view and an oblique view of the main components of an analysis container depicting an embodiment of the present invention.
Figure 20B:
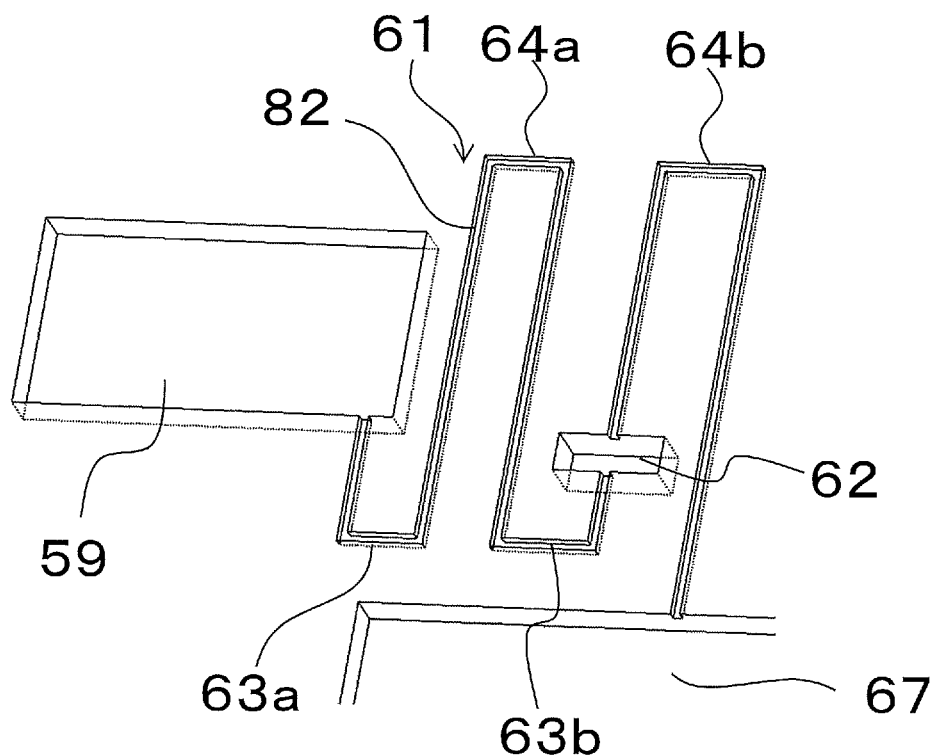

FIG. 20A is a top view of a synchronization passage, and FIG. 20B is an oblique view of the synchronization passage.

As shown in FIG. 20B, the liquid passage 61 exiting the first chamber 59 is disposed so as to pass by the upper face side of the main body 1a. The valve mechanism 62 provided along the liquid passage 61 is provided so there will be a groove that is deeper toward the lower face side than the liquid passage 61.

Figure 21A:
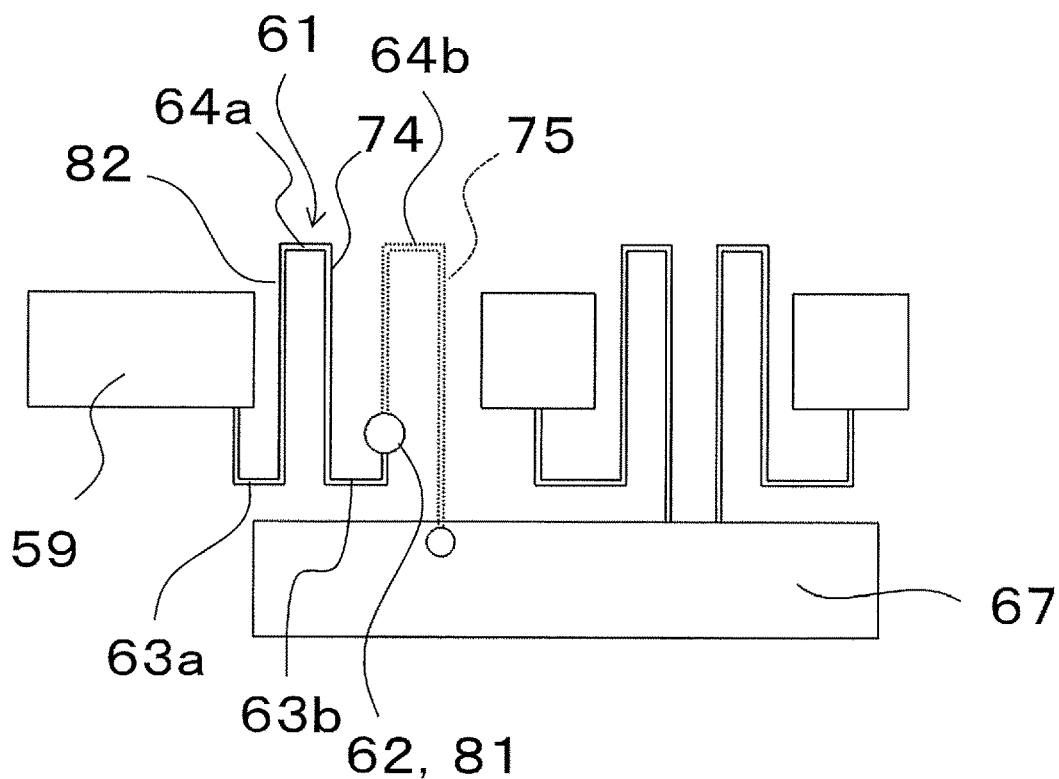
FIGS. 21A and 21B are a top view and an oblique view of the main components of an analysis container depicting an embodiment of the present invention.
Figure 21B:
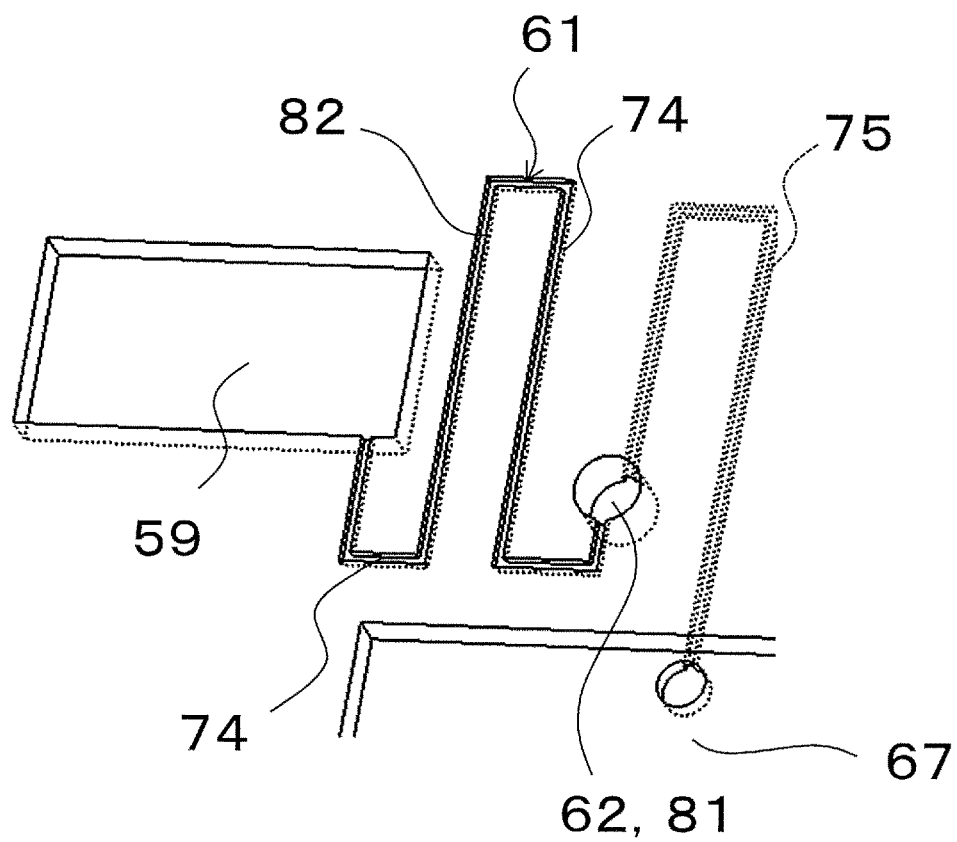

FIG. 21A is a top view of the synchronization passage, and FIG. 21B is an oblique view of the synchronization passage.

The liquid passage 61 exiting the first chamber 59 has a lead-out passage 74 from the first chamber 59 to the valve mechanism 62, and a lead-in passage 75 from the valve mechanism 62 to the mixing chamber 67.

The lead-out passage 74, as shown in FIG. 21B, is disposed to go by the upper surface of the main body 1a, and is connected to the upper end of the valve mechanism 62 including a first passage 81.

As shown in FIG. 21B, the lead-in passage 75 is connected to the lower end of the first passage 81, goes past the lower face of the main body 1a, and is connected to the mixing chamber 67.

The first passage 81 has a substantially circular lateral cross sectional shape.

Figure 22A:
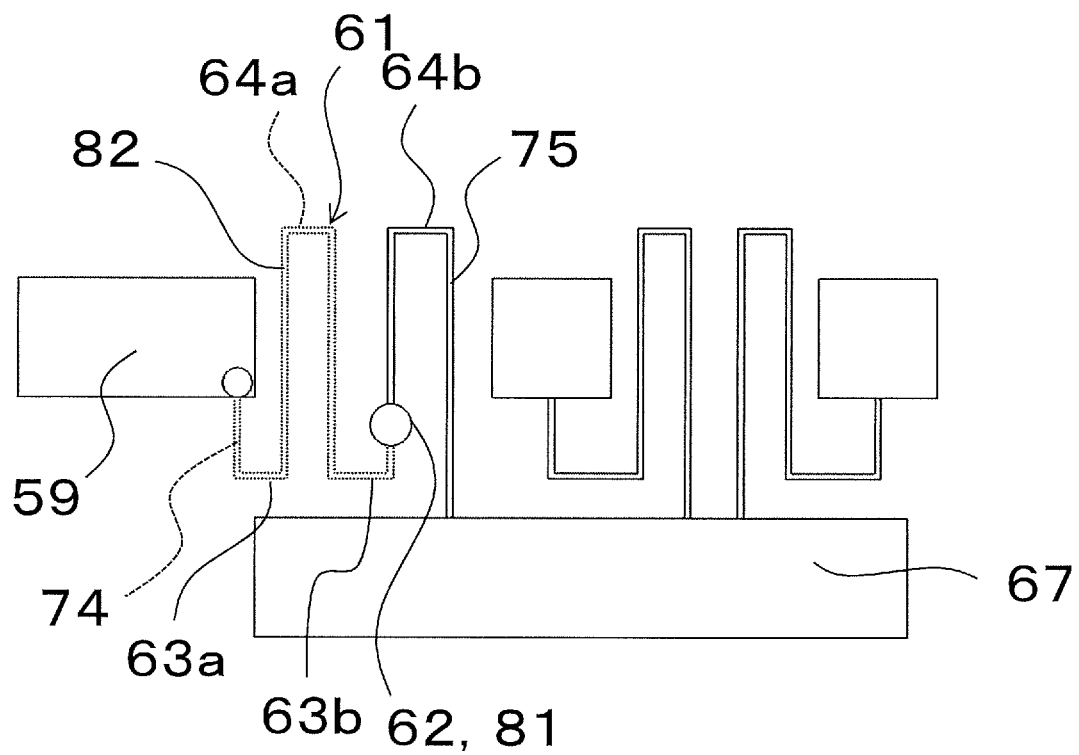
FIGS. 22A and 22B are a top view and an oblique view of the main components of an analysis container depicting an embodiment of the present invention.
Figure 22B:
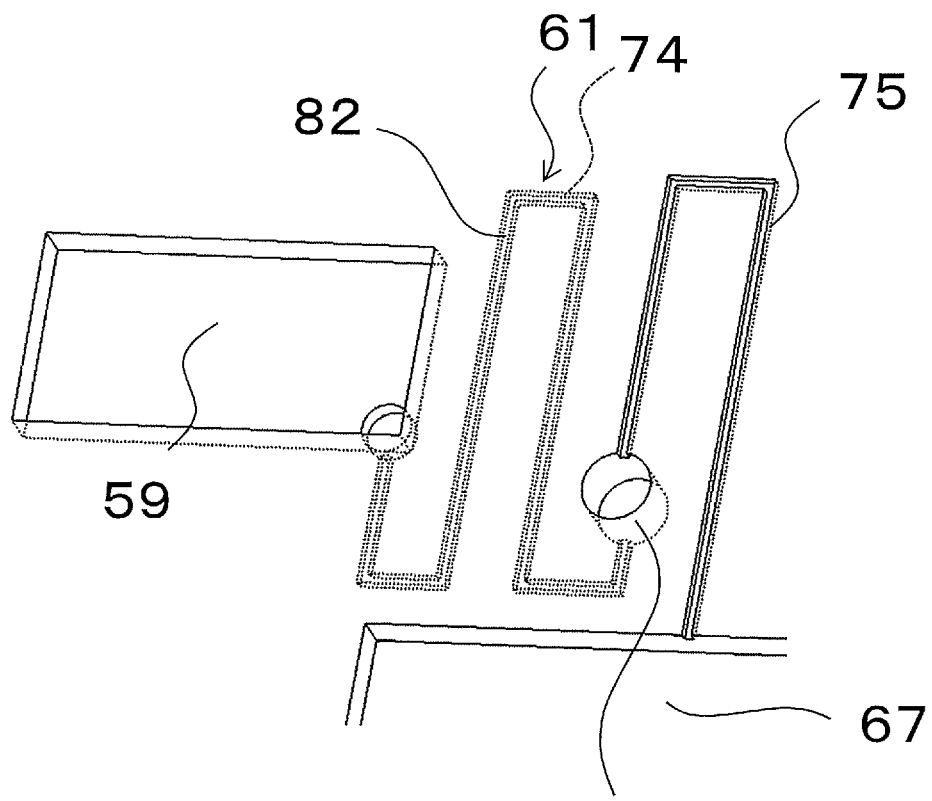

FIG. 22A is a top view of the synchronization passage, and FIG. 22B is an oblique view of the synchronization passage.

The liquid passage 61 exiting the first chamber 59 has the lead-out passage 74 from the first chamber to the valve mechanism 62, and the lead-in passage 75 from the valve mechanism 62 to the mixing chamber 67.

The lead-out passage 74 is disposed so as to pass by the lower face side of the main body 1a, and is connected to the lower end of the valve mechanism 62 including the first passage 81.

The lead-in passage 75 is connected to the upper end of the first passage, goes past the upper face of the main body 1a, and is connected to the mixing chamber 67.

The first passage 81 has a substantially circular lateral cross sectional shape.

As discussed above, this embodiment comprises the main body 1a of the analysis container 1, the first chamber 59, the mixing chamber 67, the liquid passage 61, the valve mechanism 62, and the rotational center 43 provided inside the main body 1a.

The first chamber 59 is provided in the main body 1a, and holds a liquid sample.

The liquid passage 61 connects the mixing chamber 67 with the first chamber 59, and moves the liquid sample from the first chamber 59 to the mixing chamber 67. The liquid passage 61 is configured to combine a plurality of siphon-shaped passages 82 including a valley portion 63a where the liquid passage 61 exiting the first chamber 59 protrudes radially outward (as viewed from the rotational center 43), and a peak portion 64a that passes through the valley portion 63a and then protrudes back toward the rotational center 43 side.

The valve mechanism 62 is provided along the liquid passage 61 and adjusts the movement of the liquid sample in the liquid passage 61. The valve mechanism 62 is provided at a midway position from the valley portions 63a and 63b toward the peak portions 64a and 64b along the passage 82.

This makes it possible to reduce the space taken up by the passage system in the analysis container 1.

That is, with the analysis container 1 in this embodiment, the valve mechanism 62 is disposed at a midway position from the valley portions 63a and 63b toward the peak portions 64a and 64b along the siphon-shaped passage 82.

Therefore, the liquid sample can be reliably temporarily stopped at the position of the valve mechanism 62, and the liquid sample can be held along on the liquid passage 61.

Thus using a combination of the controlling the movement of the liquid sample with the valve mechanism 62 and a centrifugal force operation (rotational operation of the analysis container 1) allows the movement of the liquid sample to be controlled in steps, in a state in which the liquid sample is held along the liquid passage 61. As a result, the passage system takes up less space in the analysis container 1.

The analysis container pertaining to a first invention comprises:
a main body;
a first chamber that is provided inside the main body and holds a liquid sample;
a second chamber that is provided inside the main body;
a liquid passage that connects the first chamber and the second chamber and moves the liquid sample from the first chamber to the second chamber;
a valve mechanism that is provided to the liquid passage and adjusts the movement of the liquid sample in the liquid passage;
a lead-out passage that is provided to the liquid passage and is connected to the first chamber; and
a first passage that is provided to the valve mechanism, is linked to the lead-out passage, and extends along the vertical direction.

The analysis container pertaining to a second invention is the analysis container pertaining to the first invention, wherein the lead-out passage has a capillary passage that moves a liquid by the surface tension of capillary action.

The analysis container pertaining to a third invention is the analysis container pertaining to the first or second invention, wherein the lead-out passage is connected at a first end to the first chamber, extends away from the rotational center provided in the main body, and is connected at a second end, which is on the opposite side from the first end, to the first passage.

The analysis container pertaining to a fourth invention is the analysis container pertaining to any of the first to third inventions, wherein the first passage has a substantially circular lateral cross sectional shape.

The analysis container pertaining to a fifth invention is the analysis container pertaining to any of the first to fourth inventions, wherein the lead-out passage is connected below the first chamber, goes past the lower side of the main body, and is connected to the first passage.

The analysis container pertaining to a sixth invention is the analysis container pertaining to the fifth invention, wherein the liquid passage has a lead-in passage that is linked at a first end to the first passage, and is connected at a second end which is on the opposite side from the first end, to the second chamber, and the lead-in passage goes by the upper side of the main body and is connected above the second chamber.

The analysis container pertaining to a seventh invention is the analysis container pertaining to any of the first to fourth inventions, wherein the lead-out passage is connected above the first chamber, goes by the upper side of the main body, and is connected to the first passage.

The analysis container pertaining to the eighth invention is the analysis container pertaining to the seventh invention, wherein the liquid passage has a lead-in passage that is linked at a first end to the first passage and is connected at a second end, on the opposite side from the first end, to the second chamber, and the lead-in passage goes by the lower side of the main body and is connected under the second chamber.

The analysis container pertaining to the ninth invention is the analysis container pertaining the any of the fifth to eighth inventions, wherein the lead-in passage has a capillary passage that moves the liquid sample by surface tension produced by capillary action.

The analysis container pertaining to the tenth invention is the analysis container pertaining to the sixth invention, wherein the surface area of a lateral cross section of the first passage is larger than that of the lead-in passage and the lead-out passage.

The analysis container pertaining to the eleventh invention comprises:

a main body;

a first chamber that is provided inside the main body and holds a liquid sample;

a second chamber that is provided inside the main body;

a liquid passage that connects the first chamber and the second chamber and moves the liquid sample from the first chamber to the second chamber;

a valve mechanism that is provided along the liquid passage and adjusts the movement of the liquid sample in the liquid passage; and a rotational center that is provided inside the main body, wherein the liquid passage is such that the passage exiting the first chamber has a siphon-shaped passage including a valley portion that protrudes radially outward when viewed from the rotational center, and a peak portion that protrudes back toward the rotational center side after passing through the valley portion, and the valve mechanism is disposed at a position on the liquid passage from the valley portion toward the peak portion.

The analysis container according to the twelfth invention is the analysis container according to the eleventh invention, wherein the valve mechanism is disposed at a position that is far away from the rotational center in the radial direction with respect to the first chamber.

The analysis container according to the thirteenth invention is the analysis container according to the twelfth invention, wherein the liquid passage is disposed so as to pass by the upper side of the main body, and the valve mechanism provided along the liquid passage is provided so there a deep groove is formed lower than the liquid passage.

The analysis container according to the fourteenth invention is the analysis container according to the twelfth invention, wherein the valve mechanism has a first passage that extends downward in the vertical direction, the liquid passage is formed so as to include a lead-out passage from the first chamber to the valve mechanism, and a lead-in passage from the valve mechanism to the second chamber, the lead-out passage goes by the upper side of the main body and is connected to the upper side of the first passage, and the lead-in passage is connected to the lower side of the first passage, goes by the lower side of the main body, and is connected to the second chamber.

The analysis container according to the fifteenth invention is the analysis container according to the eleventh or twelfth invention, wherein the valve mechanism has a first passage that extends upward in the vertical direction, the liquid passage is configured to include a lead-out passage from the first chamber to the valve mechanism and a lead-in passage from the valve mechanism to the second chamber, the lead-out passage goes by the lower side of the main body and is connected to the lower side of the first passage, and the lead-in passage is connected to the upper side of the first passage, goes by the upper side of the main body, and is connected to the second chamber.

The analysis container according to the sixteenth invention is the analysis container according to the fourteenth or fifteenth invention, wherein first passage has a substantially circular lateral cross sectional shape.

The analysis container according to the seventeenth invention is the analysis container according to any of the fourteenth to sixteenth inventions, wherein the surface area of a lateral cross section of the first passage is larger than the surface area of a lateral cross section of the lead-in passage or the lead-out passage.

The analysis container according to the eighteenth invention is the analysis container according to any of the eleventh to seventeenth inventions, wherein the liquid passage moves the liquid sample by surface tension produced by capillary action.

The analysis container pertaining to the nineteenth invention is the analysis container pertaining to any of the eleventh to eighteenth inventions, wherein the valley portion of the liquid passage is provided at a position that is far away in the radial direction as viewed from the rotational center, and the peak portion of the liquid passage is provided at a position that is near in the radial direction as viewed from the rotational center.

The analysis container pertaining the twentieth invention is the analysis container pertaining to any of the eleventh to nineteenth inventions, wherein the first chamber can hold the liquid sample, and with respect to the height of the liquid level of the first chamber when the liquid sample has moved to the outer peripheral side in the radial direction under the centrifugal force generated during rotation around the rotational center:

the valley portion of the liquid passage is provided at a position that is far away in the radial direction as viewed from the rotational center, and the peak portion of the liquid passage is provided at a position that is near in the radial direction as viewed from the rotational center.

The analysis container pertaining to the twenty-first invention, comprising:

a main body;

a dispensing chamber that dispenses a liquid sample; and a quantitative chamber that is connected to the dispensing chamber and holds the dispensed liquid sample, wherein the connecting portions of the dispensing chamber and the quantitative chamber are provided with inlet through which the liquid sample flows into the quantitative chamber, and outlets through which the liquid sample flows out of the quantitative chamber, and the inlets and the outlets function as surface tension valves.

The analysis container pertaining to the twenty-second invention is the analysis container pertaining to the twenty-first invention, further comprising a reaction chamber in which the liquid sample in the quantitative chamber is reacted with a reagent used for biochemical analysis, wherein the quantitative chamber and the reaction chamber are connected by a capillary passage.

The analysis container pertaining to the twenty-third invention is the analysis container pertaining to the twenty-first or twenty-second invention, further comprising partition walls provided to the connecting portions of the dispensing chamber and the quantitative chamber, wherein the inlets and outlets are provided at both ends of the partition walls.

The analysis container pertaining to the twenty-fourth invention is the analysis container pertaining to any of the twenty-first to twenty-third inventions, wherein the dispensing chamber is formed in an arc shape around a rotational center provided to the main body, and the quantitative chamber extends in a comb shape toward the outer peripheral side in the radial direction.

The analysis container pertaining to the twenty-fifth invention is the analysis container pertaining to any of the twenty-first to twenty-fourth inventions, wherein a plurality of the quantitative chambers are disposed on substantially the same circumference around the rotational center provided to the main body.

The analysis container pertaining to the twenty-sixth invention is the analysis container pertaining to the twenty-third invention, wherein a plurality of the partition walls are disposed on substantially the same circumference around the rotational center provided to the main body.

The analysis container pertaining to the twenty-seventh invention is the analysis container pertaining to any of the twenty-first to twenty-sixth inventions, wherein a plurality of the inlets and outlets are disposed on substantially the same circumference around the rotational center provided to the main body.

The analysis container pertaining to the twenty-eighth invention comprises:

a rotatable main body;

an insertion opening into which a specimen provided to the main body is poured and into which a specimen collecting tool can be inserted;

a specimen extraction chamber for extracting the specimen poured in through the insertion opening; and a holder that is provided to the sample extraction chamber and holds the specimen collecting tool.

The analysis container pertaining to the twenty-ninth invention is the analysis container pertaining to the twenty-eighth invention, wherein the holder holds a swab.

The analysis container pertaining to the thirtieth invention is the analysis container pertaining to the twenty-eighth or twenty-ninth invention, wherein the holder has protrusions provided at positions around the outside with respect to the rotational center of the main body, and specimen extraction chamber inner walls that are provided at positions around the inside and sandwich the specimen collecting tool in between the protrusions.

The analysis container pertaining to the thirty-first invention is the analysis container pertaining to any of the twenty-eighth to thirtieth inventions, further comprising a lid that covers the insertion opening, wherein the lid has on its inner face side a guide that comes into contact with and holds the specimen collecting tool.

The analysis container pertaining to the thirty-second invention is the analysis container pertaining to any of the twenty-eighth to thirty-first inventions, further comprising a reaction chamber for mixing the specimen extracted from the specimen extraction chamber with a reagent.

INDUSTRIAL APPLICABILITY

With the analysis container of the present invention, the analysis container can be sealed, and a liquid sample in the analysis container can be moved between chambers, so this invention is expected to find heavy application as a sealed analysis container in genetic analysis applications involving gene amplification.

REFERENCE SIGNS LIST 1 analysis container
1a main body
2 swab
2a tip portion
3 insertion opening
4 measurement device
4a cap (lid)
5 analysis container loading tray
6 analysis container base
7 upper film
8 chamber
9 lower film
10, 10a, 10b filling port
11 sealing member
12 rotary shaft insertion hole
13 specimen extraction chamber
14 specimen quantitative chamber
15 liquid passage
16 vent passage (air passage)
17 overflow chamber
18 passage
19 mixing chamber
20 capillary passage
21 specimen dilution chamber
22 blank chamber
23 liquid passage
24 vent passage
25 capillary passage
26 reagent loading chamber 27 dispensing chamber
28a, 28b, 28c quantitative chamber
29 overflow chamber
30 trap chamber
31 reservoir
32a, 32b, 32c reaction chamber
33a, 33b, 33c pump chamber
34 vent passage
35a, 35b protrusion (holder)
36 inner wall (holder, specimen extraction chamber inner wall)
37 guide
38 valve mechanism
39 first chamber
40 second chamber
41 liquid passage
41a valley portion
41b peak portion
42 vent passage (air passage)
43 rotational center
44 connection point
46a, 46b, 46c, 46d valve mechanism
47a, 47b, 47c, 47d capillary passage
48a, 48b, 48c, 48d first passage
49 second passage
50 connection point
51 connection point
51a opening
52 valve mechanism
53a lead-out passage
53b lead-in passage
54 valve mechanism
54a, 54b first passage
56a, 56b, 56c inlet
57a, 57b, 57c outlet
58a, 58b, 58c partition wall
59 first chamber
61 liquid passage
62 valve mechanism
63a, 63b valley portion
64a, 64b peak portion
65 third chamber
66 fourth chamber
67 mixing chamber
68 siphon passage
68a valley portion
68b peak portion
69 siphon passage
69a valley portion
69b peak portion
70, 71, 72, 73 point
74 lead-out passage
75 lead-in passage
76 capillary passage
77 reservoir
80 first wall
81 first passage
82 passage

The invention claimed is:

1. An analysis container, comprising:
a main body;
a rotational center provided within the main body;
a first chamber that is provided inside the main body and holds a liquid sample;
a second chamber that is provided inside the main body;
a liquid passage that connects the first chamber and the second chamber and allows the liquid sample to move from the first chamber to the second chamber by capillary force of the liquid passage and centrifugal force generated when the main body rotates around the rotational center;
an air passage that connects the first chamber and the second chamber, wherein the air passage allows air to move from the second chamber to the first chamber in a volume equivalent to a volume of the liquid sample to be moved from the first chamber; and
a first valve mechanism provided to the air passage and controlling a movement of air in the air passage,
the first valve mechanism including a capillary passage intervening between the first chamber and the air passage and allowing the liquid sample to be put into the capillary passage from the first chamber by capillary force of the capillary passage when a rotation of the main body is stopped.

2. The analysis container according to claim 1, further comprising:
a second valve mechanism that is provided to the liquid passage and adjusts a movement of the liquid sample within the liquid passage; and
a lead-out passage that is provided to the liquid passage and is connected to the first chamber,
the second valve mechanism including a first passage that is linked to the lead-out passage, and extends in a vertical direction.

3. The analysis container according to claim 1, further comprising:
a second valve mechanism that is provided to the liquid passage and adjusts a movement of the liquid sample in the liquid passage,
wherein the liquid passage is such that the passage exiting the first chamber has a siphon-shaped passage including a valley portion that protrudes radially outward when viewed from the rotational center, and a peak portion that protrudes back toward the rotational center side after passing through the valley portion, and
the second valve mechanism includes a groove or a first passage, the groove or the first passage being deeper than the liquid passage and being disposed at a position on the liquid passage from the valley portion toward the peak portion.

4. The analysis container according to claim 1,
wherein a connection point between the first chamber and the liquid passage is at a position that is farther away from the rotational center provided in the approximate center of the main body than a connection point between the first chamber and the air passage.

5. The analysis container according to claim 1,
wherein the liquid passage moves the liquid sample by a surface tension of capillary action.

6. The analysis container according to claim 1,
wherein the first valve mechanism has a first passage that is linked to the capillary passage and extends in a vertical direction.

7. The analysis container according to claim 6,
wherein the capillary passage is connected at a first end to the first chamber, extends from the first end toward the rotational center, and is connected at a second end, which is on an opposite side from the first end, to the first passage.

8. The analysis container according to claim 6,
wherein the first passage has first and second opposite ends, the first end of the first passage being connected to the first chamber, and the second end of the first passage being connected to the capillary passage, the capillary passage extending from the first passage toward the rotational center.

9. The analysis container according to claim 8, further comprising a second passage that extends in a vertical direction, wherein the capillary passage is connected to the second passage.

10. The analysis container according to claim 9, wherein the second passage has a substantially circular lateral cross sectional shape.

11. The analysis container according to claim 6, wherein the first passage has a substantially circular lateral cross sectional shape.

12. The analysis container according to claim 6, further comprising a second passage that extends in the vertical direction, wherein a surface area of a lateral cross section of the first passage and/or the second passage is larger than that of the capillary passage.

13. The analysis container according to claim 1, wherein the first chamber has a first wall surface perpendicular to a rotation direction around the rotational center provided in the approximate center within the main body, and a connection point between the first chamber and the air passage is provided near a corner of an inner periphery of the first wall surface in the first chamber.

\* \* \* \* \*